(12) United States Patent
Resconi et al.

(10) Patent No.: US 6,608,224 B2
(45) Date of Patent: Aug. 19, 2003

(54) CATALYST SYSTEM FOR THE POLYMERIZATION OF OLEFINS

(75) Inventors: Luigi Resconi, Ferrara (IT); Simona Guidotti, Casalecchio di Reno (IT)

(73) Assignee: Basell Polyolefine GmbH, Wesseling (DE)

( * ) Notice: Subject to any disclaimer, the term of this patent is extended or adjusted under 35 U.S.C. 154(b) by 11 days.

(21) Appl. No.: 09/790,314

(22) Filed: Feb. 22, 2001

(65) Prior Publication Data

US 2002/0038036 A1 Mar. 28, 2002

(30) Foreign Application Priority Data

Feb. 24, 2000 (EP) .............................................. 00200649

(51) Int. Cl.[7] .............................. C07F 5/02; C07F 5/00; C07F 17/00
(52) U.S. Cl. ............................ 556/27; 556/53; 526/127; 526/134; 526/160; 526/161; 526/943; 526/157; 502/103; 502/117; 502/152; 502/155
(58) Field of Search ............................... 502/155, 103, 502/117, 152; 526/127, 133, 134, 160, 161, 943, 157; 556/53, 27

(56) References Cited

U.S. PATENT DOCUMENTS

| | | | | |
|---|---|---|---|---|
| 5,145,819 | A | 9/1992 | Winter et al. ................ | 502/117 |
| 5,324,800 | A | 6/1994 | Welborn, Jr. et al. ........ | 526/160 |
| 5,556,928 | A | 9/1996 | Devore et al. ............... | 526/127 |
| 6,232,260 | B1 * | 5/2001 | Nagy et al. .................. | 502/155 |

FOREIGN PATENT DOCUMENTS

| | | | | |
|---|---|---|---|---|
| EP | 0129368 | 12/1984 | ........... | C08F/10/00 |
| EP | 0416815 | 3/1991 | ........... | C08F/10/00 |
| EP | 0420436 | 4/1991 | ............. | C07F/7/00 |
| EP | 0485820 | 5/1992 | ........... | C08F/4/602 |
| EP | 0485822 | 5/1992 | ........... | C08F/4/602 |
| EP | 0485823 | 5/1992 | ........... | C07F/17/00 |
| EP | 0643066 | 3/1995 | ........... | C07F/17/00 |
| EP | 0671404 | 9/1995 | ........... | C07F/17/00 |
| WO | 9623010 | 8/1906 | ......... | C08F/210/16 |
| WO | 9102012 | 2/1991 | ........... | C08F/110/02 |
| WO | 9104257 | 4/1991 | ............. | C07F/7/00 |
| WO | 9622995 | 8/1996 | ........... | C07F/17/00 |
| WO | 9627439 | 9/1996 | ........... | B01J/31/18 |
| WO | 9702298 | 1/1997 | ........... | C08F/10/02 |
| WO | 9822486 | 5/1998 | ........... | C07F/17/00 |
| WO | 9840374 | 9/1998 | ......... | C07D/319/02 |
| WO | 9921899 | 5/1999 | ........... | C08F/10/02 |
| WO | 9924446 | 5/1999 | ........... | C07F/17/00 |
| WO | 9958539 | 11/1999 | ........... | C07F/17/00 |
| WO | 9964476 | 12/1999 | ........... | C08F/4/603 |

OTHER PUBLICATIONS

B. Temme et al., Journal of Organometallic Chemistry, 488: 177–182 (1995).
M. Brookhart et al., J. Am. Chem. Soc., 120: 4049–4050 (1998).
M. Brookhart et al., J. Am. Chem. Soc., 117: 6414–6415 (1995).
M. Brookhart et al., J. Am. Chem. Soc., 118: 267–268 (1996).
V. Gibson et al., Chem. Commun., 849–851 (1998).
F. Jager et al., Chem. Ber./Recueil., 130 (3), p. 399–403 (1997).
C. Carman et al., Macromolecules, 10: 536–544 (1977).
J. Randall, Macromol. Chem. Phys., C29: 201–317 (1989).
I. Tritto et al., Macromolecules, 28: 3342–3350 (1995).
M. Kakugo et al., Macromolecules, 15: 1150–1152 (1982).
B. Temme et al., J. of Organometallic Chemistry, 488: 177–182 (1995).
D. Röttger et al., J. of Organometallic Chemistry, 518: 17–19 (1996).
Eker et al., European Journal Inorganic Chemistry 2001 (published online: Jan. 5, 2001), 535–538.*
Klosin et al., J. Am. Chem. Soc. 2000, vol. 122, 9560–9561.*

* cited by examiner

Primary Examiner—David W. Wu
Assistant Examiner—R. Harlan

(57) ABSTRACT

An organometallic compound obtainable by contacting
  a) a compound having the following formula (I):

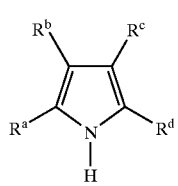

(I)

wherein $R^a$, $R^b$, $R^c$ and $R^d$ equal to or different from each other are hydrocarbon groups
  b) a Lewis acid of formula (II)

$$MtR^1{}_3 \qquad (II)$$

wherein Mt is a metal belonging to Group 13 of the Periodic Table of the Elements (IUPAC); $R^1$, equal to or different from each other, are selected from the group consisting of halogen, halogenated $C_6$–$C_{20}$ aryl and halogenated $C_7$–$C_{20}$ alkylaryl groups; two $R^1$ groups can also form with the metal Mt one condensed ring.

These compounds are useful as cocatalysts for polymerizing olefins.

10 Claims, No Drawings

CATALYST SYSTEM FOR THE POLYMERIZATION OF OLEFINS

FIELD OF THE INVENTION

The present invention relates to organometallic compounds a to catalyst systems for the polymerization of olefins comprising such organometallic compounds. The invention also relates to a process for the polymerization of olefins carried out in the presence of the above catalyst system.

PRIOR ART DISCLOSURE

Homogeneous catalytic systems based on metallocene complexes are known to be active in the polymerization of olefins; said complexes must be activated by means of suitable cocatalytic compounds.

The first generation of cocatalysts developed for homogeneous metallocene olefin polymerization consisted of alkyl aluminum chlorides ($AlR^5Cl$), wherein substituents R are preferably methyl or ethyl; these cocatalysts exhibit low ethylene polymerization activity levels and negligible propylene polymerization activity.

The second generation of cocatalyst systems comprised the class of alkylalumoxanes, commonly obtained by reacting trialkyl aluminum compound and water in a molar ratio of 1:1 to 100:1; these alumoxanes are oligomeric linear and/or cyclic compounds represented by the formulae:

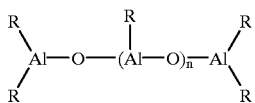

for linear oligomeric alumoxanes, and

for cyclic oligomeric alumoxanes, wherein the substituents R are usually methyl, ethyl or isobutyl groups, n ranges from 0 to 40, and m ranges from 3 to 40. Methylalumoxane (MAO) is the most widely used cocatalyst.

Nevertheless alkylalumoxanes, and in particular methylalumoxane, though very active in metallocene-based catalyst systems, exhibit several inherent problems in use, such as the need for high alumoxane/metallocene molar ratios to produce satisfactory catalytic activities, their high reactivity toward impurities (moisture, alcohols etc.) and their easy flammability. Moreover, it has not been possible to isolate characterizable metallocene active species using MAO. Accordingly, some of the developments in this area involved a search for alternative cocatalysts. $B(C_6F_5)_4^-$ types of non-coordinating anions have been developed as cocatalysts for metallocene-based systems. More specifically, these activators are ion-exchange compounds comprising a trialkyl or dialkylammonium cation, which will irreversibly react with a metallocene, and a fluorinated arylborate anion, capable of stabilizing the metallocene cation complex and sufficiently labile to permit displacement by ethylene during polymerization (see for instance WO 91/02012). In particular, they have the advantage of being used in a 1:1 catalyst-cocatalyst ratio. Therefore, it is usually not necessary to remove the small amount of boron from the final polymer, unlike the aluminum-based cocatalysts mentioned above. As preferred activators are tri(n-butyl)ammonium tetrakis(pentafluorophenyl)boron and N,N-dimethylanilinium tetrakis(pentafluorophenyl)boron.

These cocatalysts exhibit high catalytic activities but, from a synthetic point of view, the industrial production of these cocatalysts is quite expensive.

Finally, these $B(C_6F_5)_4^-$ anions are generally used in the form of the corresponding ammonium salts, thus leading to the release of aminic by-products in consequence of the metallocene activation. In addition they have a low solubility in the polymerization solvents.

The fourth generation of cocatalysts is $B(C_6F_5)_3$. The anion $MeB(C_6F_5)_3^-$ formed after $Me^-$ abstraction from the metallocene dimethyl complex is weakly coordinated to the electrondeficient metal center, thus resulting in a decrease of the catalytic activity and in addition the catalyst system is not stable.

An alternative route for using $B(C_6F_5)_3$ has been proposed by B. Temme in Journal of Organometallic Chemistry 488 (1995) 177–182. Bis cyclopentadienyl methyl pyrrolidyl zirconocene has been treated with $B(C_6F_5)_3$ with the formation of the pyrrolydyl borate and the metallocene cation. In this paper it is reported that the obtained salt is catalytically active and polymerizes ethylene even if with a moderate activity.

WO 99/64476 describes a process for the preparation of polyolefins by using a catalyst system comprising a metallocene compound, a Lewis acid-base complex and a tri-n-alkylaluminum compound. As described at page 4 and illustrated in the figures the function of the Lewis base is to inhibit the reaction between the metallocene compounds and the Lewis acid. Only upon addition of the tri-n-alkylaluminum compound the catalyst system becomes active. This catalyst system does not solve completely the problems of the use $B(C_6F_5)_3$, for the reason that the anion that is weakly coordinated to the electrondeficient metal center is always of the type $MeB(C_6F_5)_3^-$ and therefore the active catalyst system is not stable for a long time.

Therefore, there is still the need for alternative cocatalysts, easy to prepare, that form a stable catalyst system and able to exert good activities in the polymerization of olefins.

The Applicant has now found a new class of olefin polymerization cocatalysts, which reduces the use of excess of cocatalyst with respect to alkylaluminoxanes, does not lead to the release of undesired by-products after the metallocene activation, and provides stable catalytic compositions.

The present invention concerns an organometallic compound obtainable by contacting a) a compound having the following formula (I):

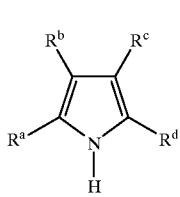

(I)

wherein $R^a$, $R^b$, $R^c$ and $R^d$ equal to or different from each other are selected from the group consisting of hydrogen, halogen, linear or branched, saturated or unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^a$, $R^b$, $R^c$ and $R^d$ form one or more $C_4$–$C_7$ rings, optionally containing O, S, N, P or Si atoms, that can bear substituents; with b) a Lewis acid of formula (II)

$$MtR^1_3 \qquad (II)$$

wherein Mt is a metal belonging to Group 13 of the Periodic Table of the Elements (IUPAC); $R^1$, equal to or different from each other, are selected from the group consisting of halogen, halogenated $C_6$–$C_{20}$ aryl and halogenated $C_7$–$C_{20}$ alkylaryl groups; two $R^1$ groups can also form with the metal Mt one condensed ring, such as for example 9-borafluorene compounds.

Preferably Mt is B or Al, and more preferably is B; The substituents $R^1$ are preferably selected from the group consisting of $C_6F_5$, $C_6F_4H$, $C_6F_3H_2$, $C_6H_3(CF_3)_2$, perfluoro-biphenyl, heptafluoro-naphthyl, hexafluoro-naphthyl and pentafluoro-naphthyl; Most preferred $R^1$ substituents are $C_6F_5$ radicals.

Preferred organometallic compounds are those belonging to the following two classes (1) and (2), having respectively formula (III) and (IV).

Class (1)

Organometallic compounds belonging to class (1) have the following formula (III)

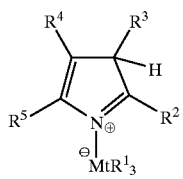

(III)

wherein
Mt is a metal belonging to Group 13 of the Periodic Table of the Elements (IUPAC); $R^1$, equal to or different from each other, are selected from the group consisting of halogen, halogenated $C_6$–$C_{20}$ aryl and halogenated $C_7$–$C_{20}$ alkylaryl groups; two $R^1$ groups can also form with the metal Mt one condensed ring, such as for example 9-borafluorene compounds; and the substituents $R^5$, $R^4$, $R^3$ and $R^2$ equal to or different from each other, are selected from the group consisting of hydrogen, halogen, linear or branched, saturated or unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^2$–$R^5$ form one or more $C_4$–$C_7$ rings, optionally containing O, S, N, P or Si, preferably when the substituents $R^2$–$R^5$ form one or more rings, $R^4$ and $R^5$ form one $C_4$–$C_7$ aromatic ring, optionally containing O, S, N, or P atoms, that can bear substituents; and $R^2$ and $R^3$ form one non aromatic $C_4$–$C_7$ ring, optionally containing O, S, N, P or Si atoms; with the proviso that at least one of $R^2$, $R^3$, $R^4$ and $R^5$ is different from hydrogen.

Preferably in the organometallic compounds of formula (III) Mt is B or Al, and more preferably is B; the substituents $R^1$ equal to or different from each other, are preferably selected from the group consisting of $C_6F_5$, $C_6F_4H$, $C_6F_3H_2$, $C_6H_3(CF_3)_2$, perfluoro-biphenyl, heptafluoro-naphthyl, hexafluoro-naphthyl and pentafluoro-naphthyl; even more preferably, $R^1$ is $C_6F_5$; at least one of the substituents $R^5$ and $R^4$ are preferably a $C_6$–$C_{20}$ aryl, $C_7$–$C_{20}$ arylalkyl and $C_7$–$C_{20}$ alkylaryl groups, optionally containing O, S, N P, Si or halogen atoms or together they can form an aromatic $C_4$–$C_7$ ring optionally containing O, S, N or P atoms, that can bear substituents.

A preferred subclass of organometallic compounds of formula (III) is that of formula (V):

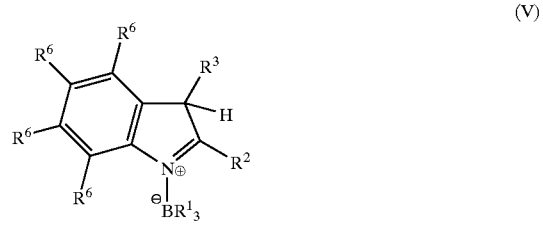

(V)

wherein
B is a boron atom;
the substituents $R^1$, $R^3$ and $R^2$ have the meaning reported above and the substituents $R^6$, the same or different from each other, are selected from the group consisting of hydrogen, halogen, linear or branched, saturated or unsaturated, $C_{1-C10}$ alkyl, $C_6$–$C_{20}$ aryl, $C_7$–$C_{20}$ arylalkyl and $C_7$–$C_{20}$ alkylaryl groups optionally containing O, S, N, P, Si or halogen atoms, or two or more adjacent substituents $R^6$ form one or more $C_4$–$C_7$ optionally containing O, S, N, P or Si atoms rings that can bear substituents; preferably $R^6$ are selected from the group consisting of hydrogen, halogen, linear or branched, saturated or unsaturated $C_1$–$C_{10}$ alkyl. Preferably $R^2$ and $R^3$ are hydrogen. Another preferred subclass of organometallic compounds of formula (III) is that of formula (VI):

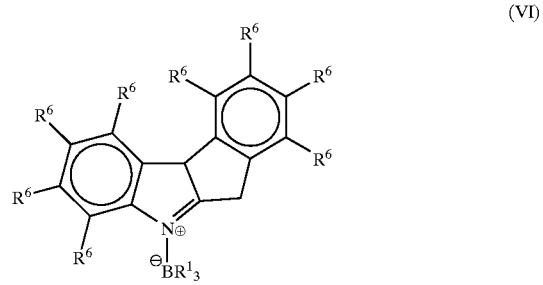

(VI)

wherein the substituents $R^1$ and $R^6$ have the meaning reported above.

Class (2)

Organometallic compound belonging to class (2) have the following formula (IV):

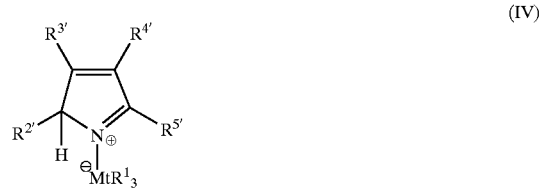

(IV)

wherein
Mt and $R^1$ are defined as above;
the substituents $R^{2'}$, $R^{3'}$, $R^{4'}$ and $R^{5'}$ equal to or different from each other, are selected from the group consisting of hydrogen, halogen, linear or branched, saturated or unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^{2'}$, $R^{3'}$, $R^{4'}$ and $R^{5'}$ form one or more $C_4$–$C_7$ rings optionally containing O, S, N, P or Si atoms, that can bear substituents; said rings can be aliphatic or optionally can contain double bonds, with the proviso that said rings are not aromatic.

Preferably the substituents $R^{2'}$, $R^{3'}$, $R^{4'}$ and $R^{5'}$ equal to or different from each other, are selected from the group consisting of hydrogen, linear or branched, saturated or unsaturated, $C_1$–$C_{10}$ alkyl, optionally containing O, S, N, P, Si or halogen atoms, or two or more adjacent substituents $R^{2'}$, $R^{3'}$, $R^{4'}$ and $R^{5'}$ form one or more $C_4$–$C_7$ rings optionally containing O, S, N, P or Si atoms, that can bear substituents; said rings can be aliphatic or optionally can contains double bonds, with the proviso that said rings are not aromatic;

A preferred subclass of organometallic compounds of formula (IV) is that of formula (VII):

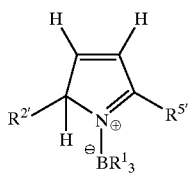

(VII)

wherein
the substituents $R^1$ have the meaning described above and the substituents $R^{2'}$ and $R^{5'}$ equal to or different from each other are $C_1$–$C_{20}$ alkyl; preferably they are methyl or ethyl groups.

Non limitative examples of compounds belonging to formula (I) are:
pyrrole; ethyl 3,5-dimethyl-2-pyrrolecarboxylate; tert-butyl 3,4,5-trimethyl-2-pyrrole carboxylate; ethyl 3, 4-diethyl-5-methyl-2-pyrrole carboxylate; tert-butyl 4-acetyl-3,5 dimethyl-2-pyrrole carboxylate; diethy 3,4-pyrroledicarboxylate; 2-ethylpyrrole; 2,4-dimethylpyrrole; 2,5-dimethylpyrrole; 4,5,6,7-tetrahydroindole; 1,2,5-trimethylpyrrole; 2,4-dimethyl-3-ethylpyrrole; 3-acetyl-2,4-dimethylpyrrole; 3-ethyl-2-methyl-1,5,6,7-tetrahydro-4-H-indol-4-one; 2-acetylpyrrole; 2-(trichloroacetyl)pyrrole; 1,5, 6,7-tetrahydro-4h-indol-4-one; 2-(trifluoroacetyl)pyrrole; pyrrole-2-carboxaldehyde; indole; 2-methylindole; 3-methylindole; 4-methylindole; 5-methylindole; 6-methylindole; 7-methylindole; 2,3-dimethylindole; 2,5-dimethylindole; 5-fluoroindole; 4-chloroindole; 5-chloroindole; 6-chloroindole; 5-chloro-2-methylindole; 5-bromoindole; 5-methoxyindole; 4-methoxyindole; 5-acetoxy-2-methylindole; 5,6-dimethoxyindole; 5-benzyloxyindole; 4-nitroindole; 5-nitroindole; 3-acetylindole; 3-(trifluoroacetyl)indole; indole-3-carboxyaldehyde; 2-methylindole-3-carboxyaldehyde; 5-methoxyindole-3-carboxyaldehyde; phenyl-3,3'-dimethyl-2,2'-diindolyl-methane, 3-indolyl acetate; 4-indolyl acetate; methyl indole-4-carboxylate; methyl 4-methoxy-2-indolecarboxylate; 3-cyanoindole; 5-cyanoindole; 7-azaindole.

Example of Lewis acid of formula (II) are:
tris(pentafluorophenyl)borane;tris(heptafluoronaphthyl) borane; tris(2,3,5,6,7,8-hexafluoronaphthyl)borane; tris(2,4, 5,6,7,8-hexafluoronaphthyl)borane; tris(3,4,5,6,7,8-hexafluoronaphthyl)borane; tris(2,3,4,6,7,8-hexafluoronaphthyl)borane; tris(2,3,4,5,7,8-hexafluoronaphthyl)borane; tris(2,3,5,6,7,8-hexafluoro-4-methylnaphthyl)borane; tris(2,4,5,6,7,8-hexafluoro-3-methylnaphthyl)borane; tris(3,4,5,6,7,8-hexafluoro-2-methylnaphthyl)borane; tris(2,3,4,6,7,8-hexafluoro-5-methylnaphthyl)borane; tris(2,3,4,5,7,8-hexafluoro-6-methylnaphthyl)borane; tris(nonafluorobiphenyl)borane; tris(2,2',3,3',5,5',6,6'-octafluorobiphenyl)borane; tris(3,3',4, 4',5,5',6,6'-octafluorobiphenyl)borane; tris(2,2',4,4',5,5',6,6'-octafluorobiphenyl)borane; tris(2,2',3,3',4,4',6,6'-octafluorobiphenyl)borane; tris(2,2',3,3',4,4',5,5'-octafluorobiphenyl)borane; tris(2,2',3,3',5,5',6,6'-octafluorobiphenyl)borane; tris(3,3',4,4',5,5',6,6'-octafluorobiphenyl)borane; tris(2,2',4,4',5,5',6,6'-octafluorobiphenyl)borane; tris(2,2',3,3',4,4',6,6'-octafluoro-5,5'-methylbiphenyl)borane; tris(2,2',3,3',4,4',5,5'-octafluoro-6,6'-methylbiphenyl)borane; tris(2,2',3,3',5,5',6, 6'-octafluoro-4,4'-biphenyl)borane; tris(3,3',4,4',5,5',6,6'-octafluoro-2,2'-biphenyl)borane; tris(2,2',4,4',5,5',6,6'-octafluoro-3,3'-biphenyl)borane; tris(2,3,4,6-tetrafluorophenyl)borane; tris(2,3,5,6-tetrafluorophenyl) borane; tris(2,3,5-trifluorophenyl)borane, tris(2,3,6-trifluorophenyl)borane; tris(1,3-difluorophenyl)borane, tris (2,3,5,6-tetrafluoro-4-methylphenyl)borane; tris(2,3,4,6-tetrafluoro-5-methylphenyl)borane; tris(2,6-difluoro-3-methylphenyl)borane; tris(2,4-difluoro-5-methylphenyl) borane; tris(3,5-difluoro-2-methylphenyl)borane; fluorobis (pentafluorophenyl)borane; chlorobis(pentafluorophenyl) borane; dichloro(pentafluorophenyl)borane; difluoro (pentafluorophenyl)borane; 9-chloro-9-boroperfluorofluorene; 9-methyl-9-boroperfluorpfluorene; 9-pentafluorophenyl-9-oroperfluorofluorene and 9-bromo-9-boroperfluorofluorene.

It is another object of the present invention a catalyst system for the polymerization of olefins comprising the product obtained by contacting:
(A) at least one transition metal organometallic compound, pyrrolidyl bis(η- cyclopentadienyl)methylzirconium being excluded and,
(B) an organometallic compound obtainable by contacting
a) a compound having the following formula (I):

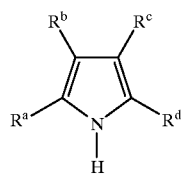

(I)

wherein $R^a$, $R^b$, $R^c$ and $R^d$ equal to or different from each other are selected from the group consisting of hydrogen, halogen, linear or branched, saturated or unsaturated, $C_1$-$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^a$, $R^b$, $R^c$ and $R^d$ form one or more $C_4$–$C_7$ rings, optionally containing O, S, N, P or Si atoms, that can bear substituents; with
b) a Lewis acid of formula (II)

$$MtR^1_3 \qquad (II)$$

wherein Mt is a metal belonging to Group 13 of the Periodic Table of the Elements (IUPAC); $R^1$, equal to or different from each other, are selected from the group consisting of halogen, halogenated $C_6$–$C_{20}$ aryl and halogenated $C_7$–$C_{20}$ alkylaryl groups; two $R^1$ groups can also form with the metal Mt one condensed ring, such as for example 9-borafluorene compounds; and (C) optionally an alkylating agent.

Preferably the catalyst system for the polymerization of olefins comprises the product obtained by contacting:
(A) at least one transition metal organometallic compound, pyrrolidyl bis(η- cyclopentadienyl)methylzirconium being excluded;
(B) an organometallic compound belonging to class (1) (compounds of formula (III), (V), and (VI)) or class (2) (compounds of formula (IV) and (VII)) as described above; and
(C) optionally an alkylating agent.

Transition metal organometallic compounds for use in the catalyst system in accordance with the present invention are compounds suitable as olefin polymerization catalysts by coordination or insertion polymerization. The class includes known transition metal compounds useful in traditional Ziegler-Natta coordination polymerization, the metallocene compounds similarly and the late transition metal compounds known to be useful in coordination polymerization. These will typically include Group 4–10 transition metal compounds wherein at least one metal ligand can be abstracted by the catalyst activators. As a rule, when said ligand is hydrogen or an hydrocarbyl group containing from 1 to 20 carbon atoms optionally containing silicon atoms, the transition metal organometallic catalyst compounds can be used as such, otherwise an alkylating agent has to be used in order to alkylate said catalyst. The alkylation can be carried out in a separate step or in situ.

The alkylating agent is a compound able to react with the transition metal organometallic catalyst compounds and exchange said ligand that can be abstracted, with an alkyl group. Preferably said alkylating agent is selected from the group consisting of $R^{10}Li$, $R^{10}Na$, $R^{10}K$, $R^{10}MgU$ or $AlR^{10}_{3-z}W_z$, or alumoxanes, wherein $R^{10}$ can be $C_1$–$C_{10}$ alkyl, alkenyl or alkylaryl radicals, optionally containing one or more Si or Ge atoms, z is 0, 1 or 2 or a non integer number ranging from 0 to 2; U is chlorine, bromine or iodine and W is hydrogen or chlorine, bromine or iodine atom; non-limiting examples of $R^{10}$ are methyl, ethyl, butyl and benzyl; non limiting example of $AlR^{10}_{3-z}W_z$ compounds are trimethylaluminum (TMA), tris(2,4,4-trimethyl-pentyl) aluminum (TIOA), tris(2-methyl-propyl)aluminum (TIBA), tris(2,3,3-trimethyl-butyl)aluminum, tris(2,3-dimethyl-hexyl)aluminum, tris(2,3-dimethyl-butyl)aluminum, tris(2,3-dimethyl-pentyl)aluminum, tris(2,3-dimethyl-heptyl) aluminum, tris(2-methyl-3-ethyl-pentyl)aluminum and tris (2-ethyl-3,3-dimethyl-butyl). Non limiting example of alumoxanes are: methylalumoxane (MAO), tetra-(isobutyl) alumoxane (TIBAO), tetra-(2,4,4-trimethyl-pentyl) alumoxane (TIOAO), tetra-(2,3 -dimethylbutyl)alumoxane (TDMBAO) and tetra-(2,3,3-trimethylbutyl)alumoxane (TTMBAO).

Different from the catalyst system disclosed in WO 99/64476, the catalyst system of the present invention is stable and can be isolated.

A preferred class of transition metal organometallic compounds are metallocene compounds belonging to the following formula (VIII)

$(Cp)(ZR^7_m)_n(A)_rML_p$  (VIII)

wherein $(ZR^7_m)_n$ is a divalent group bridging Cp and A; Z being C, Si, Ge, N or P, and the $R^7$ groups, equal to or different from each other, being hydrogen or linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl groups or two $R^7$ can form a aliphatic or aromatic $C_4$–$C_7$ ring;

Cp is a substituted or unsubstituted cyclopentadienyl group, optionally condensed to one or more substituted or unsubstituted, saturated, unsaturated or aromatic rings, containing from 4 to 6 carbon atoms, optionally containing one or more heteroatoms;
A is O, S, $NR^8$, $PR^8$ wherein $R^8$ is hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl, or A has the same meaning of Cp;
M is a transition metal belonging to group 4, 5 or to the lanthanide or actinide groups of the Periodic Table of the Elements (IUPAC version);
the substituents L, equal to or different from each other, are monoanionic sigma ligands selected from the group consisting of hydrogen, halogen, $R^9$, $OR^9$, $OCOR^9$, $SR^9$, $NR^9_2$ and $PR^9_2$. wherein $R^9$ is a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl group, optionally containing one or more Si or Ge atoms; preferably, the substituents L are the same;
m is 1 or 2, and more specifically it is 1 when Z is N or P, and it is 2 when Z is C, Si or Ge;
n is an integer ranging from 0 to 4;
r is 0, 1 or 2; preferably 0 or 1; n is 0 when r is 0;
p is an integer equal to the oxidation state of the metal M minus r+1; i.e. minus 3 when r=2, minus 2 when r=1, and minus 1 when r=0, and ranges from 1 to 4.

In the metallocene compound of formula (VIII), the divalent bridge $(ZR^7_m)_n$ is preferably selected from the group consisting of $CR^7_2$, $(CR^7_2)_2$, $(CR^7_2)_3$, $SiR^7_2$, $GeR^7_2$, $NR^7$ and $PR^7$, $R^7$ having the meaning reported above; more preferably, said divalent bridge is $Si(CH_3)_2$, $SiPh_2$, $CH_2$, $(CH_2)_2$, $(CH_2)_3$ or $C(CH_3)_2$.

The variable m is preferably 1 or 2; the variable n ranges preferably from 0 to 4 and, when n>1, the atoms Z can be the same or different from each other, such as in divalent bridges $CH_2$—O, $CH_2$—S and $CH_2$—Si(CH_3)_2$.

The ligand Cp, which is π-bonded to said metal M, is preferably selected from the group consisting of cyclopentadienyl, mono-, di-, tri- and tetra-methyl cyclopentadienyl; 4-$^t$butyl-cyclopentadienyl; 4-adamantyl-cyclopentadienyl; indenyl; mono-, di-, tri- and tetra-methyl indenyl; 2-methyl indenyl, 3-$^t$butyl-indenyl, 4-phenyl indenyl, 4,5 benzo indenyl; 3-trimethylsilyl-indenyl; 4,5,6, 7-tetrahydroindenyl; fluorenyl; 5,10-dihydroindeno[1,2-b] indol-10-yl; N-methyl- or N-phenyl-5,10-dihydroindeno [1,2-b]indol-10-yl; 5,6-dihydroindeno[2,1-b]indol-6-yl; N-methyl-or N-phenyl-5,6-dihydroindeno[2,1-b]indol-6-yl; azapentalene-4-yl; thiapentalene-4-yl; azapentalene-6-yl; thiapentalene-6-yl; mono-, di- and tri-methyl-azapentalene-4-yl, 2,5-dimethyl-cyclopenta[1,2-b :4,3-b']-dithiophene.

The group A is O, S, $N(R^8)$, wherein $R^8$ is hydrogen, a linear or branched, saturated or unsaturated $C_1$–$C_{20}$ alkyl, $C_3$–$C_{20}$ cycloalkyl, $C_6$–$C_{20}$ aryl, $C_7$–$C_{20}$ alkylaryl or $C_7$–$C_{20}$ arylalkyl, preferably $R^8$ is methyl, ethyl, n-propyl, isopropyl, n-butyl, t-butyl, phenyl, p-n-butyl-phenyl, benzyl, cyclohexyl and cyclododecyl; more preferably $R^8$ is t-butyl; or A has the same meaning of Cp.

Non limiting examples of compounds belonging to formula (VIII) are the rac and meso form (when present) of the following compounds:
bis(cyclopentadienyl)zirconium dimethyl;
bis(indenyl)zirconium dimethyl;
bis(tetrahydroindenyl)zirconium dimethyl;
bis(fluorenyl)zirconium dimethyl;
(cyclopentadienyl)(indenyl)zirconium dimethyl;
(cyclopentadienyl)(fluorenyl)zirconium dimethyl;

(cyclopentadienyl)(tetrahydroindenyl)zirconium dimethyl;
(fluorenyl)(indenyl)zirconium dimethyl;
dimethylsilanediylbis(indenyl)zirconium dimethyl,
dimethylsilanediylbis(2-methyl-4-phenylindenyl)zirconium dimethyl,
dimethylsilanediylbis(4-naphth ylindenyl)zirconium dimethyl,
dimethylsilanediylbis(2-methylindenyl)zirconium dimethyl,
dimethylsilanediylbis(2-methyl4-t-butylindenyl)zirconium dimethyl,
dimethylsilanediylbis(2-methyl-4-isopropylindenyl) zirconium dimethyl,
dimethylsilanediylbis(2,4-dimeth ylindenyl)zirconium dimethyl,
dimethylsilanediylbis(2-methyl-4,5-benzoindenyl) zirconium dimethyl,
dimethylsilanediylbis(2,4,7-trimethylindenyl)zirconium dimethyl,
dimethylsilanediylbis(2,4,6-trimethylindenyl)zirconium dimethyl,
dimethylsilanediylbis(2,5,6-trimethylindenyl)zirconium dimethyl,
methyl(phenyl)silanediylbis(2-methyl-4,6-diisopropylindenyl)-zirconium dimethyl,
methyl(phenyl)silanediylbis(2-methyl-4-isopropylindenyl)-zirconium dimethyl,
1,2-ethylenebis(indenyl)zirconium dimethyl,
1,2-ethylenebis(4,7-dimethylindenyl)zirconium dimethyl,
1,2-ethylenebis(2-methyl-4-phenylindenyl)zirconium dimethyl,
1,4-butanediylbis(2-methyl-4-phenylindenyl)zirconium dimethyl,
1,2- ethylenebis(2-methyl-4,6-diisopropylindenyl) zirconium dimethyl,
1,4-butanediylbis(2-methyl-4-isopropylindenyl)zirconium dimethyl,
1,4-butanediylbis(2-methyl-4,5-benzoindenyl)zirconium dimethyl,
1,2- ethylenebis (2-methyl-4,5-benzoindenyl)zirconium dimethyl,
[4-($\eta^5$-cyclopentadienyl)-4,6,6-trimethyl($\eta^5$-4,5-tetrahydropentalene)]dimethylzirconium,
[4-($\eta^5$-3'-trimethylsilylcyclopentadienyl)-4,6,6-trimethyl ($\eta^5$-4,5-tetrahydropentalene)]dimethylzirconium,
(tert-butylamido)(tetramethyl-$\eta^5$-cyclopentadienyl)-1,2-ethanedimethyltitanium,
(methylamido)(tetramethyl-$\eta^5$-cyclopentadienyl) dimethylsilyldimethyltitanium,
(methylamido)(tetramethyl-$\eta^5$-cyclopentadienyl)-1,2-ethanediyldimethyltitanium,
(tertbutylamido)-(2,4-dimethyl-2,4-pentadien-1-yl) dimethylsilyldimethyltitanium,
bis(1,3-dimethylcyclopentadienyl)zirconium dimethyl,
methylene(3-methyl-cyclopentadienyl)-7-(2,5-dimethylcyclopentadienyl-[1,2-b:4,3-b']dithiophene) zirconium dimethyl;
methylene(3-isopropyl-cyclopentadienyl)-7-(2,5-dimethylcyclopentadienyl-[1,2-b:4,3-b']dithiophene) zirconium dimethyl and dimethyl;
methylene(2,4-dimethyl-cyclopentadienyl)-7-(2,5-dimethylcyclopentadienyl-[1,2-b:4,3-b']dithiophene) zirconium dimethyl and dimethyl;
methylene(2,3,5-trimethyl-cyclopentadienyl)-7-(2,5-dimethylcyclopentadienyl-[1,2-b:4,3-b']dithiophene) zirconium dimethyl and dimethyl;
methylene-1-(indenyl)-7-(2,5-dimethylcyclopentadienyl-[1,2-b:4,3-b']dithiophene)zirconium dimethyl and dimethyl;
methylene-1-(indenyl)-7-(2,5-ditrimethylsilylcyclopentadienyl-[1,2-b:4,3-b'] dithiophene)zirconium dimethyl and dimethyl;
methylene-1-(3-isopropyl-indenyl)-7-(2,5-dimethylcyclopentadienyl-[1,2-b:4,3-b']dithiophene) zirconium dimethyl and dimethyl;
methylene- 1-(2-methyl-indenyl)-7-(2,5-dimethylcyclopentadienyl-[1,2-b:4,3-b']dithiophene) zirconium dimethyl and dimethyl;
methylene-1-(tetrahydroindenyl)-7-(2,5-dimethylcyclopentadienyl-[1,2-b:4,3-b']dithiophene) zirconium dimethyl and dimethyl;
methylene(2,4-dimethyl-cyclopentadienyl)-7-(2,5-dimethylcyclopentadienyl-[1,2-b:4,3-b']dioxazol) zirconium dimethyl and dimethyl;
methylene(2,3, 5-trimethyl-cyclopentadienyl)-7-(2,5-dimethylcyclopentadienyl-[1,2-b:4,3-b']dioxazol) zirconium dimethyl and dimethyl;
methylene-1-(indenyl)-7-(2,5-dimethylcyclopentadienyl-[1,2-b:4,3-b']dioxazol)zirconium dimethyl and dimethyl;
isopropylidene(3-methyl-cyclopentadienyl)-7-(2,5-dimethylcyclopentadienyl-[1,2-b: 4,3 -b']dithiophene) zirconium dimethyl and dimethyl;
isopropylidene(2,4-dimethyl-cyclopentadienyl)-7-(2,5-dimethylcyclopentadienyl-[1,2-b: 4,3 -b']dithiophene) zirconium dimethyl and dimethyl;
isopropylidene(2,4-diethyl-cyclopentadienyl)-7-(2,5-dimethylcyclopentadienyl-[1,2-b:4,3-b']dithiophene) zirconium dimethyl and dimethyl;
isopropylidene(2,3,5-trimethyl-cyclopentadienyl)-7-(2,5-dimethylcyclopentadienyl-[1,2-b:4,3-b']dithiophene) zirconium dimethyl and dimethyl;
isopropylidene-1-(indenyl)-7-(2,5-dimethylcyclopentadienyl-[1,2-b:4,3 -b']dithiophene) zirconium dimethyl and dimethyl;
isopropylidene-1-(2-methyl-indenyl)-7-(2,5-dimethylcyclopentadienyl-[1,2-b :4,3 -b']dithiophene) zirconium dimethyl and dimethyl;
dimethylsilandiyl- 1-(2-methyl-indenyl)-7-(2,5-dimethylcyclopentadienyl-[1,2-b:4,3 -b']dithiophene) hafnium dimethyl and dimethyl;
dimethylsilanediyl(3-tert-butyl-cyclopentadienyl)(9-fluorenyl)zirconium dimethyl,
dimethylsilanediyl(3-isopropyl-cyclopentadienyl)(9-fluorenyl)zirconium dimethyl,
dimethylsilanediyl(3-methyl-cyclopentadienyl)(9-fluorenyl)zirconium dimethyl,
dimethylsilanediyl(3-ethyl-cyclopentadienyl)(9-fluorenyl) zirconium dimethyl,
1-2-ethane(3-tert-butyl-cyclopentadienyl)(9-fluorenyl) zirconium dimethyl,
1-2-ethane (3-isopropyl-cyclopentadienyl)(9-fluorenyl) zirconium dimethyl,
1-2-ethane (3-methyl-cyclopentadienyl)(9-fluorenyl) zirconium dimethyl,
1-2-ethane (3-ethyl-cyclopentadienyl)(9-fluorenyl) zirconium dimethyl,
dimethylsilandiylbis-6-(3-methylcyclopentadienyl-[1,2-b]-thiophene) dimethyl;
dimethylsilandiylbis-6-(4-methylcyclopentadienyl-[1,2-b]-thiophene)zirconium dimethyl;
dimethylsilandiylbis-6-(4-isopropylcyclopentadienyl-[1,2-b]-thiophene)zirconium dimethyl;
dimethylsilandiylbis-6-(4-ter-butylcyclopentadienyl-[1,2-b]-thiophene)zirconium dimethyl;
dimethylsilandiylbis-6-(3-isopropylcyclopentadienyl-[1,2-b]-thiophene)zirconium dimethyl;

dimethylsilandiylbis-6-(3-phenylcyclopentadienyl-[1,2-b]-thiophene)zirconium dimethyl;
dimethylsilandiylbis-6-(2,5-dimethyl-3-phenylcyclopentadienyl-[1,2-b]-thiophene)zirconium dimethyl;
dimethylsilandiylbis-6-[2,5-dimethyl-3-(2-methylphenyl)cyclopentadienyl-[1,2-b]-thiophene]zirconium dimethyl;
dimethylsilandiylbis-6-[2,5-dimethyl-3-(2,4,6-trimethylphenyl)cyclopentadienyl-[1,2-b]-thiophene]zirconium dimethyl;
dimethylsilandiylbis-6-[2,5-dimethyl-3-mesitylenecyclopentadienyl-[1,2-b]-thiophene]zirconium dimethyl;
dimethylsilandiylbis-6-(2,4,5-trimethyl-3-phenylcyclopentadienyl-[1,2-b]-thiophene)zirconium dimethyl;
dimethylsilandiylbis-6-(2,5-diethyl-3-phenylcyclopentadienyl-[1,2-b]-thiophene)zirconium dimethyl;
dimethylsilandiylbis-6-(2,5-diisopropyl-3-phenylcyclopentadienyl-[1,2-b]-thiophene)zirconium dimethyl;
dimethylsilandiylbis-6-(2,5-diter-butyl-3-phenylcyclopentadienyl-[1,2-b]-thiophene)zirconium dimethyl;
dimethylsilandiylbis-6-(2,5-ditrimethylsilyl-3-phenylcyclopentadienyl-[1,2-b]-thiophene)zirconium dimethyl;
dimethylsilandiylbis-6-(3-methylcyclopentadienyl-[1,2-b]-silole)zirconium dimethyl;
dimethylsilandiylbis-6-(3-isopropylcyclopentadienyl-[1,2-b]-silole)zirconium dimethyl;
dimethylsilandiylbis-6-(3-phenylcyclopentadienyl-[1,2-b]-silole)zirconium dimethyl;
dimethylsilandiylbis-6-(2,5-dimethyl-3-phenylcyclopentadienyl-[1,2-b]-silole)zirconium dimethyl;
dimethylsilandiylbis-6-[2,5-dimethyl-3-(2-methylphenyl)cyclopentadienyl-[1,2-b]-silole]zirconium dimethyl;
dimethylsilandiylbis-6-[2,5-dimethyl-3-(2,4,6-trimethylphenyl)cyclopentadienyl-[1,2-b]-silole]zirconium dimethyl;
dimethylsilandiylbis-6-[2,5-dimethyl-3-mesitylenecyclopentadienyl-[1,2-b]-silole]zirconium dimethyl;
dimethylsilandiylbis-6-(2,4,5-trimethyl-3-phenylcyclopentadienyl-[1,2-b]-silole)zirconium dimethyl;
[dimethylsilyl(tert-butylamido)][(N-methyl-1,2-dihydrocyclopenta[2,1-b]indol-2-yl)]titanium dimethyl;
[dimethylsilyl(tert-butylamido)][(6-methyl-N-methyl-1,2-dihydrocyclopenta[2,1-b]indol-2-yl)]titanium dimethyl;
[dimethylsilyl(tert-butylamido)][(6-methoxy-N-methyl-1,2-dihydrocyclopenta[2,1-b]indol-2-yl)]titanium dimethyl;
[dimetbylsilyl(tert-butylamido)][(N-ethyl-1,2-dihydrocyclopenta[2,1-b]indol-2-yl)]titanium dimethyl;
[dimethylsilyl(tert-butylamido)][(N-phenyl-1,2-dihydrocyclopenta[2,1-b]indol2-yl)]titanium dimethyl;
[dimethylsilyl(tert-butylamido)][(6-methyl-N-phenyl-1,2-dihydrocyclopenta[2,1-b]indol2-yl)]titanium dimethyl;
[dimethylsilyl(tert-butylamido)][(6-methoxy-N-phenyl-1,2-dihydrocyclopenta[2,1-b]indol2-yl)]titanium dimethyl;
[dimethylsilyl(tert-butylamido)][(N-methyl-3,4-dimethyl-1,2-dihydrocyclopenta[2,1-b]indol-2-yl)]titanium dimethyl;
[dimethylsilyl(tert-butylamido)][(N-ethyl-3,4-dimethyl-1,2-dihydrocyclopenta[2,1-b]indol-2-yl)]titanium dimethyl;
[dimethylsilyl(tert-butylamido)][(N-phenyl-3,4-dimethyl-1,2-dihydroclopenta[2,1-b]indol-2-yl)]titanium dimethyl;

as well as the corresponding dichloro, hydrochloro and dihydro compounds and the corresponding $\eta^4$-butadiene compounds.

When A is $N(R^8)$, a suitable class of metallocene complexes (A) for use in the catalysts complexes of the invention comprises the well-known constrained geometry catalysts, as described in EP-A-0 416 815, EP-A-0 420 436, EP-A-0 671 404, EP-A-0 643 066 and WO-A-91/04257.

According to a preferred embodiment of the invention, the group A has the same meaning of Cp, and is preferably substituted or unsubstituted cyclopentadienyl, indenyl, tetrahydroindenyl (2,5-dimethyl-cyclopenta[1,2-b:4,3-b']-dithiophene).

Suitable metallocene complexes that may be used in the catalyst system according to the present invention are described in WO 98/22486, WO 99/58539 WO 99/24446, U.S. Pat. No. 5,556,928, WO 96/22995, EP-485822, EP-485820, U.S. Pat. No. 5,324,800 and EP-A-0 129 368.

The metal M is preferably Ti, Zr or Hf, and more preferably Zr.

The substituents L are preferably the same and are selected from the group consisting of halogens, $R^9$, $OR^9$ and $NR^9{}_2$; wherein $R^9$ is a $C_1$–$C_7$ alkyl, $C_6$–$C_{14}$ aryl or $C_7$–$C_{14}$ arylalkyl group, optionally containing one or more Si or Ge atoms; more preferably, the substituents L are selected from the group consisting of —Cl, —Br, —Me, —Et, —n-Bu, —sec-Bu, —Ph, —Bz, —CH$_2$SiMe$_3$, —OEt, —OPr, —OBu, —OBz and —NMe$_2$, even more preferably L is methyl.

The integer n ranges from 0 to 4, and it is preferably 1 or 2.

When n=0 and r=1, A can have only the meaning of Cp; Cp and A are preferably pentamethyl cyclopentadienyl, indenyl or 4,5,6,7-tetrahydroindenyl groups.

Non-limiting examples of these metallocene complexes are:

| | | |
|---|---|---|
| (Me$_3$Cp)$_2$MCl$_2$ | (Me$_4$Cp)$_2$MCl$_2$ | (Me$_5$Cp)$_2$MCl$_2$ |
| (EtMe$_4$Cp)$_2$MCl$_2$ | [(C$_8$H$_5$)Me$_4$Cp]$_2$MCl$_2$ | (Et$_5$Cp)$_2$MCl$_2$ |
| (Ind)$_2$MCl$_2$ | (H$_4$Ind)$_2$MCl$_2$ | (Me$_4$Cp)(Me$_5$Cp)MCl$_2$ |
| [(Si(CH$_3$)$_3$Cp]$_2$MCl$_2$ | (Me$_5$Cp)MCl$_3$ | (Ind)MCl$_3$ |
| (H$_4$Ind)MCl$_3$ | | | and the corresponding —MMe$_2$, —M(OMe)$_2$, —MH$_2$, —MHCl, —MMeOMe, —MmeOEt, —MMeOCH$_2$Ph, —MMeOPh —M(OEt)$_2$, —MCl(OMe), —MCl(OEt), —MPh$_2$, —MBz$_2$, —MMeCl, —MPhCl, —M(NMe$_2$)$_2$ and —M(NMe$_2$)OMe derivatives, wherein Me=methyl, Et=ethyl, Cp=cyclopentadienyl, Ind=indenyl, H$_4$Ind=4,5,6,7-tetrahydroindenyl, Ph=phenyl, Bz=benzyl, and M is preferably Zr.

When n=1 or 2 and r=1, Cp and A, same or different from each other, are preferably cyclopentadienyl, tetramethylcyclopentadienyl, indenyl, 4,5,6,7-tetra-hydro-indenyl, 2-methyl-4,5,6,7-tetra-hydro-indenyl, 4,7-dimethyl4,5,6,7-tetra-hydroindenyl, 2,4,7-trimethyl-4,5,6,7-tetra-hydro-indenyl or fluorenyl groups; $(ZR^7{}_m)_n$ is preferably Me$_2$Si, Me$_2$C, CH$_2$ or C$_2$H$_4$. Non-limiting examples of metallocene complexes of formula (II), wherein n=1 or 2 and r=1, are:

| | | |
|---|---|---|
| Me$_2$Si(Me$_4$Cp)$_2$MCl$_2$ | Me$_2$C(Me$_4$Cp)(MeCp)MCl$_2$ | Me$_2$Si(Ind)$_2$MCl$_2$ |
| C$_2$H$_4$(Ind)$_2$MCl$_2$ | C$_2$H$_4$(H$_4$Ind)$_2$MCl$_2$ | Ph(Me)Si(Ind)$_2$MCl$_2$ |
| Ph$_2$Si(Ind)$_2$MCl$_2$ | Me$_2$C(Flu)(Cp)MCl$_2$ | Me$_2$Si(Flu)(Cp)MCl$_2$ |
| C$_2$H$_4$(Me$_4$Cp)$_2$MCl$_2$ | C$_2$Me$_4$(Ind)$_2$MCl$_2$ | Me$_2$SiCH$_2$(Ind)$_2$MCl$_2$ |
| C$_2$H$_4$(2-MeInd)$_2$MCl$_2$ | C$_2$H$_4$(3-MeInd)$_2$MCl$_2$ | C$_2$H$_4$(4,7-Me$_2$Ind)$_2$MCl$_2$ |
| C$_2$H$_4$(5,6-Me$_2$Ind)$_2$MCl$_2$ | C$_2$H$_4$(2-MeH$_4$Ind)$_2$MCl$_2$ | C$_2$H$_4$(2,4,7-Me$_3$H$_4$Ind)$_2$MCl$_2$ |
| C$_2$H$_4$(4,7-Me$_2$H$_4$Ind)$_2$MCl$_2$ | C$_2$H$_4$(2,4,7-Me$_3$Ind)$_2$MCl$_2$ | C$_2$H$_4$(2-Me-benz[e]Ind)$_2$MCl$_2$ |
| C$_2$H$_4$(Benz[e]Ind)$_2$MCl$_2$ | Me$_2$Si(2-MeInd)$_2$MCl$_2$ | Me$_2$Si(4,7-Me$_2$Ind)$_2$MCl$_2$ |
| Me$_2$Si(2-Me-4-Ph-Ind)$_2$MCl$_2$ | Me$_2$Si(5,6-Me$_2$Ind)$_2$MCl$_2$ | Me$_2$Si(2,4,7-Me$_3$Ind)$_2$MCl$_2$ |
| Me$_2$Si(2-MeH$_4$Ind)$_2$MCl$_2$ | Me$_2$Si(4,7-Me$_2$H$_4$Ind)$_2$MCl$_2$ | Me$_2$Si(2,4,7-Me$_3$H$_4$Ind)$_2$MCl$_2$ |
| Me$_2$Si(Benz[e]Ind)$_2$MCl$_2$ | Me$_2$Si(2-Me-Benz[e]Ind)$_2$MCl$_2$ | Me$_2$C(Ind)$_2$MCl$_2$ |
| Me$_2$C(3-Me-Ind)$_2$MCl$_2$ | Me$_2$C(3-iPr-Ind)$_2$MCl$_2$ | Me$_2$C(3-Me$_3$Si-Ind)$_2$MCl$_2$ |
| Me$_2$C(3-tBu-Ind)$_2$MCl$_2$ | Me$_2$C(3-tBu-H$_4$Ind)$_2$MCl$_2$ | Me$_2$C(3-tBu-Cp)$_2$MCl$_2$ |
| Me$_2$C(2-Me-4-tBu-Cp)$_2$MCl$_2$ | H$_2$C(3-tBu-Ind)$_2$MCl$_2$ | H$_2$C(3-iPr-Ind)$_2$MCl$_2$ |
| H$_2$C(3-Me$_3$Si-Ind)$_2$MCl$_2$ | H$_2$C(4,7-Me$_2$Ind)$_2$MCl$_2$ | H$_2$C(1-Ph-5,7-Me$_2$Ind)$_2$MCl$_2$ |
| H$_2$C(2-Me-Ind)$_2$MCl$_2$ | H$_2$C(2-Me-3-Me$_3$Si-Ind)$_2$MCl$_2$ | H$_2$C(Ind)$_2$MCl$_2$ | and the corresponding —MMe$_2$, —M(OMe)$_2$, —M(OEt)$_2$, —MCl(OMe), —MCl(OEt), —MPh$_2$, —MBz$_2$, —MMeCl, —MPhCl, —M(NMe$_2$)$_2$ and —M(NMe$_2$)OMe derivatives, wherein Me, Cp, Ind, Flu, Ph, Bz, H$_4$Ind and M has the meanings reported above.

Suitable metallocene complexes (A) are the bridged bis-indenyl metallocenes as described for instance in U.S. Pat. No. 5,145,819 and EP-A-0 485 823.

Further metallocene complexes suitable for the catalyst system of the invention are the classes of heterocyclic metallocenes described in WO 98/22486 and WO 99/24446. Among these metallocenes, particularly preferred are the ones reported from page 15, line 8 to page 24, line 17; from page 25, line 1 to page 31, line 9; and from page 58, penultimate line, to page 63, line 20 of WO 98/22486. Other preferred metallocenes are the ones obtained from the bridged ligands listed from page 11, line 18, to page 14, line 13 of WO 99/24446

A further preferred class of transition metal organometallic catalyst compounds are late transition metal complex of formula (IX) or (X)

  (IX)

  (X)

wherein M$^a$ is a metal belonging to Group 8, 9, 10 or 11 of the Periodic Table of the Elements (new IUPAC notation); L$^a$ is a bidentate or tridentate ligand of formula (XI):

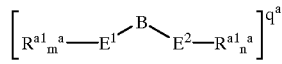   (XI)

wherein:
B is a C$_1$–C$_{50}$ bridging group linking E$^1$ and E$^2$, optionally containing one or more atoms belonging to Groups 13–17 of the Periodic Table;
E$^1$ and E$^2$, the same or different from each other, are elements belonging to Group 15 or 16 of the Periodic Table and are bonded to said metal M$^a$;
the substituents R$^{a1}$, equal to or different from each other, are selected from the group consisting of hydrogen, linear or branched, saturated or unsaturated C$_1$–C$_{20}$ alkyl, C$_3$–C$_{20}$ cycloalkyl, C$_6$–C$_{20}$ aryl, C$_7$–C$_{20}$ alkylaryl and C$_7$–C$_{20}$ arylalkyl radicals, optionally containing one or more atoms belonging to groups 13–17 of the Periodic Table of the Elements (such as B, Al, Si, Ge, N, P, O, S, F and Cl atoms); or two R$^{a1}$ substituents attached to the same atom E$^1$ or E$^2$ form a saturated, unsaturated or aromatic C$_4$–C$_7$ ring, having from 4 to 20 carbon atoms;

m$^a$ and n$^a$ are independently 0, 1 or 2, depending on the valence of E$^1$ and E$^2$, so to satisfy the valence number of E$^1$ and E$^2$; q$^a$ is the charge of the bidentate or tridentate ligand so that the oxidation state of M$^a$X$^a_p$X$^a_s$ or M$^a$A$^a$ is satisfied, and the compound (IX) or (X) is overall neutral;

X$^a$, the same or different from each other, are monoanionic sigma ligands selected from the group consisting of hydrogen, halogen, R$^a$, OR$^a$, OSO$_2$CF$_3$, OCOR$^a$, SR$^a$, —NR$^a_2$ and PR$^a_2$ groups, wherein the R$^a$ substituents are linear or branched, saturated or unsaturated, C$_1$–C$_{20}$ alkyl, C$_3$–C$_{20}$ cycloalkyl, C$_6$–C$_{20}$ aryl, C$_7$–C$_{20}$ alkylaryl or C$_7$–C$_{20}$ arylalkyl radicals, optionally containing one or more atoms belonging to groups 13–17 of the Periodic Table of the Elements (new IUPAC notation), such as B, N, P, Al, Si, Ge, O, S and F atoms; or two X$^a$ groups form a metallacycle ring containing from 3 to 20 carbon atoms; the substituents X$^a$ are preferably the same;

p$^a$ is an integer ranging from 0 to 3, so that the final compound (IX) or (X) is overall neutral; and A$^a$ is a π-allyl or a π-benzyl group.

Non limiting examples of late transition metal complexes are those described in WO 96/23010, WO 97/02298, WO 98/40374 and J.Am.Chem.Soc. 120:4049–4050, 1998. Brookhart et al, J. Am. Chem. Soc. 1995, 117, 6414 and Brookhart et al, J. Am. Chem. Soc., 1996, 118, 267, Brookhart et al, J. Am. Chem. Soc. 1998, 120, 4049, Gibson et al, Chem. Commun. 1998, 849, WO 96/27439 and Chem. Ber./Recl. (1997), 130(3), 399–403.

It is a further object of the present invention a process for the polymerization of one or more olefins in the presence of a catalyst system as described above.

The organometallic compounds according to the invention exert good activities as cocatalysts in olefin polymerization process; Moreover, they are easy to prepare and do not lead to the release of undesired by-products after the metallocene activation. Further they are stable and produce stable catalyst compositions under polymerization conditions.

The organometallic compounds of the invention are easily prepared by reacting, in about stoichiometric amounts, a compound having the formula (I):

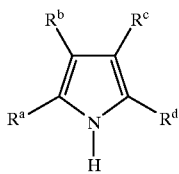

(I)

wherein $R^a$, $R^b$, $R^c$ and $R^d$ are described above; with a Lewis acid of formula (II)

$$MtR^1_3 \quad (II)$$

wherein Mt and $R^1$ are described above.

The reaction between said Lewis acid and the compound of formula (I) is preferably carried out in an aprotic solvent, even more preferably in a polar aprotic solvent (such as toluene, diethyl ether or $CH_2Cl_2$), at room temperature, the reaction can be carried out also in the presence of little amount of water, preferably equal to or less than one molar equivalent with respect to the Lewis acid. The acidity of the Lewis acid must be sufficiently high to induce the migration of a hydrogen from the N atom to the C atom in α or β-position of the pyrrole ring.

The molar ratio between the organometallic compound (B) and the transition metal organometallic catalyst compound (A), calculated as the molar ratio between the metal Mt of the Lewis acid and the metal of the transition metal organometallic catalyst compound, preferably ranges from 10:1 to 1:10, more preferably from 2:1 to 1:2, and even more preferably is about 1:1.

According to the invention, component (B) can suitably comprise a mixture of two or more organometallic compounds of the invention. Moreover, component (B) can be used in combination with other compatible cocatalysts known in the state of the art, such as alumoxane compounds.

The catalyst system of the invention may also comprise one or more aluminum compounds of formula $AlR^{10}{}_{3-z}W_z$, acting as scavenger, wherein $R^{10}$ can be $C_1$–$C_{10}$ alkyl, alkenyl or alkylaryl radicals, optionally containing one or more Si or Ge atoms, z is 0, 1 or 2 or a non integer number ranging from 0 to 2; U is chlorine, bromine or iodine atom and W is hydrogen, chlorine, bromine or iodine; non-limiting examples of aluminum compounds are trimethylaluminum (TMA), tris(2,4,4-trimethyl-pentyl)aluminum (TIOA), tris(2-methylpropyl)aluminum (TIBA), tris(2,3,3-trimethyl-butyl)aluminum, tris(2,3-dimethyl-hexyl)aluminum, tris(2,3-dimethyl-butyl)aluminum, tris(2,3-dimethyl-pentyl)aluminum, tris(2,3-dimethyl-heptyl)aluminum, tris(2-methyl-3-ethyl-pentyl)aluminum and tris(2-ethyl-3,3-dimethyl-butyl).

Another example of compound that can act as scavenger are alumoxane compounds containing at least one group of the type:

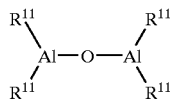

wherein the $R^{11}$ substituents, which may be the same or different, are described above. In particular, alumoxanes of the formula:

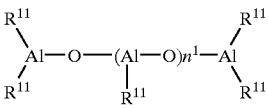

can be used in the case of linear compounds, wherein $n^1$ is 0 or an integer from 1 to 40 and the $R^{15}$ substituents are defined as above, or alumoxanes of the formula:

can be used in the case of cyclic compounds, wherein $n^2$ is an integer from 2 to 40 and the $R^{11}$ substituents are defined as above.

Examples of alumoxanes suitable as scavenger according to the present invention are metbylalumoxane (MAO), tetra-(isobutyl)alumoxane (TIBAO), tetra-(2,4,4-trimethylpentyl) alumoxane (TIOAO), tetra-(2,3-dimethylbutyl)alumoxane (TDMBAO) and tetra-(2,3,3-trimethylbutyl)alumoxane (TTMBAO).

Particularly interesting alumoxanes are those disclosed in WO 99/21899.

The catalyst system of the invention may be formed prior to its introduction into a polymerization reactor or in situ in the reactor, by contacting the above-described components (A), (B) and optionally (C).

According to an embodiment of the invention, components (A), (B) and optionally (C) are first contacted and then introduced into the reactor, wherein separately an aluminum compound $AlR^{10}{}_{3-z}W_z$, or an alumoxane has been introduced. Alternatively, components (A), (B) and optionally (C) and said aluminum compound $AlR^{10}{}_{3-z}W_z$ or said alumoxane may be contacted together prior to their introduction into the reactor.

The catalysts of the present invention can be used on inert supports. This may be achieved by depositing said transition metal organometallic catalyst compound (A), or the product of the reaction thereof with the organometallic compound (B) and optionally with the alkylating agent (C), or said organometallic compound, and subsequently said transition metal organometallic compound before or after the optional treatment with said alkylating agent, on inert supports such as silica, alumina, styrene/divinylbenzene copolymers, polyethylene or polypropylene.

The thus obtained solid compound can be suitably used in gas phase polymerization.

The catalysts of the present invention can be used in the polymerization reactions of olefins. Therefore, according to a further object, the invention provides a process for the polymerization of one or more olefins comprising contacting one or more olefins under polymerization conditions in the presence of a catalyst system as described above.

Olefins which can be polymerized with the process of the present invention are, for instance, α-olefins of formula $CH_2$=CHR, wherein R is hydrogen or a $C_1$–$C_{20}$ alkyl radical.

The catalysts according to the present invention can be conveniently used in the homopolymerization of ethylene, in particular for the preparation of HDPE, and in the copolymerization of ethylene, in particular for the preparation of LLDPE. Suitable comonomers in ethylene copolymers are α-olefins of formula $CH_2$=CHR', wherein R' is a linear, branched or cyclic $C_1$–$C_{20}$ alkyl radical or cycloolefins. Examples of such olefins are propylene, 1-butene, 1-pentene, 4-methyl-1-pentene, 1-hexene, 1-octene, allylcyclohexane, cyclopentene, cyclohexene, norbornene and 4,6-dimethyl-1-heptene.

Further suitable comonomers in said ethylene copolymers are polyenes, in particular conjugated or non-conjugated, linear or cyclic dienes, such as 1,4-hexadiene, isoprene, 1,3-butadiene, 1,5-hexadiene and 1,6-heptadiene.

When the organometallic compounds object of the present invention are used as cocatalyst in copolymerization of ethylene they generally produce a polymer having a higher molecular weight with respect to alumoxanes, in particular methylalumoxane.

The catalysts of the invention can be suitably used in propylene homopolymerization, in particular for the production of isotactic polypropylene.

Moreover, the catalysts of the invention can be suitably used in the preparation of elastomeric copolymers of ethylene with α-olefins of formula $CH_2=CHR''$, wherein R'' is a $C_1$–$C_{10}$ alkyl radical, such as propylene, 1-butene, 4-methyl-1-pentene, 1-hexene and 1-octene; said copolymers may optionally contain minor proportions of units deriving from polyenes.

According to a further embodiment, the catalysts according to the present invention are used in the preparation of cycloolefin polymers. Monocyclic and polycyclic olefin monomers can be either homopolymerized or copolymerized, also with linear olefin monomers.

The polymerization processes of the present invention can be carried out in liquid phase, optionally in the presence of an inert hydrocarbon solvent, or in gas phase. Said hydrocarbon solvent can be either aromatic (such as toluene) or aliphatic (such as propane, hexane, heptane, isobutane, cyclohexane and 2,2,4-trimethylpentane).

The polymerization temperature preferably ranges from 0° C. to 250° C.; in the preparation of HDPE and LLDPE, it is preferably comprised between 20° C. and 150° C. and, more particularly between 40° C. and 90° C.; in the preparation of elastomeric copolymers, it is preferably comprised between 0° C. and 200° C., and more preferably between 20° C. and 100° C. The molecular weight of the polymers can be varied simply by varying the polymerization temperature, the type or the concentration of the catalyst components, or by using molecular weight regulators, such as hydrogen.

The molecular weight distribution can be varied by using mixtures of different metallocene complexes or by carrying out the polymerization in several stages which differ in the polymerization temperature and/or the concentrations of molecular weight regulator.

The polymerization yield depends on the purity of the transition metal organometallic catalyst compound (A) in the catalyst, therefore, said compound can be used as such or can be subjected to purification treatments before use.

The following examples are given for illustrative and not limiting purposes.

GENERAL PROCEDURES AND CHARACTERIZATIONS

All operations were performed under nitrogen by using conventional Schlenk-line techniques. Solvents were purified by degassing with $N_2$ and passing over activated (8 hours, $N_2$ purge, 300° C.) $Al_2O_3$, and stored under nitrogen. Indole (Aldrich, purity 98% or Fluka, purity 99%), 2-methylindole (Aldrich, purity 98%), 3-methylindole (Aldrich, purity 98%), pyrrole (Aldrich, purity 98%), 2,4-dimethylpyrrole (Aldrich, purity 97%), 2,5-dimethylpyrrole (Aldrich, purity 98%), 2-ethylpyrrole (Aldrich, purity 90%), 4,5,6,7-tetrahydroindole (Aldrich, purity 98%), $BCl_3$ (Aldrich, 1.0 M solution in heptane) and $B(C_6F_5)_3$ (Boulder Scientific Company) were used as received. 2-methyl-5,6-dihydroindeno[2,1-b]indole was synthesized in our laboratory following the procedure described in patent WO 99/24446. The melting points of the compounds were obtained using a capillary Electrothermal instrument.

$^1$H-NMR and $^{13}$C-NMR

The proton and carbon spectra of the compounds were obtained using a Bruker DPX 200 spectrometer operating in the Fourier transform mode at room temperature at 200.13 MHz and 50.33 MHz respectively. The samples were dissolved in $CDCl_3$, $CD_2Cl_2$ or $C_6D_6$. As reference the residual peak of $CHCl_3$ or $CHDCl_2$ or $C_6HD_5$ in the $^1$H spectra (7.25 ppm, 5.35 ppm and 7.15 ppm, respectively) and the peak of the solvent in the $^{13}$C spectra (53.80 ppm for $CD_2Cl_2$ and 128.00 ppm for $C_6D_6$) were used. Proton spectra were acquired with a 15° pulse and 2 seconds of delay between pulses; 32 transients were stored for each spectrum. The carbon spectra were acquired with a 45° pulse and 6 seconds of delay between pulses; about 512 transients were stored for each spectrum. $CD_2Cl_2$ (Aldrich, 99.8% atom D) was used as received, while $CDCl_3$ (Aldrich, 99.8% atom D) and $C_6D_6$ (Aldrich, 99% atom D) were dried over activated 4 Å molecular sieves before use. Preparation of the samples was carried out under nitrogen using standard inert atmosphere techniques.

SYNTHESIS OF THE ORGANOMETALLIC BORON COMPOUNDS

EXAMPLE 1

N-[tris(2,3,4,5,6-pentafluorophenyl)borane]3H-indole (A-2)

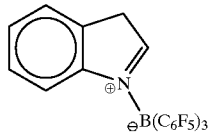

Procedure a)

Indole (99%, 1.07 g, MW=117.15, 9.0 mmol) was dissolved in 10 mL of $CH_2Cl_2$ and charged into a 50 mL Schlenk under nitrogen atmosphere. A solution of $B(C_6F_5)_3$ (4.61 g, MW=511.99, 9.0 mmol) in 25 mL of $CH_2Cl_2$ was added at room temperature under stirring. During the addition, the color of the solution turned immediately from yellowish to amber yellow; exothermicity was not observed. The reaction mixture was stirred at room temperature for 1 h, then the solvent was removed in vacuo to give a whitish solid as product (5.32 g). Yield=94.4%.

$^1$H NMR ($CD_2Cl_2$, δ, ppm): 4.30 (AB system, 2H, H3, H3 ); 7.39–7.72 (m, 4H, Ar); 8.83 (d, 1H, $J_{HF}$=5.0 Hz, H2).

$^{13}$C NMR ($CD_2Cl_2$, δ, ppm): 42.18 (C3); 118.26 (CH); 125.35 (CH); 129.16 (CH); 129.20 (CH); 133.07 (C); 147.97 (C); 175.43 (C2) (peak assigned by a DEPT experiment). m.p.=203.9° C. ≧206.7° C.

Procedure b)

A solution of indole (99%, 0.72 g, MW=117.15, 6.05 mmol) in 5 mL of $Et_2O$ was added at −20° C. under nitrogen atmosphere to a suspension of $B(C_6F_5)_3$ (99.4%, 3.13 g, MW=511.99, 6.07 mmol) in 20 mL of ethyl ether in a 50 mL Schlenk flask. During the addition the color of the suspension turned from whitish to yellow. The reaction mixture was then allowed to warm up to room temperature and stirred for 2 h with final formation of a yellow solution. A $^1$H NMR analysis showed that the reaction was already complete after 1 h stirring at room temperature. The solvent was evaporated in vacuo to give a light yellow solid as product (yield 100%).

$^1$H NMR (CDCl$_3$, δ, ppm): 4.22 (broad AB system, 2H, H3, H3'); 7.34–7.66 (m, 4H, Ar); 8.77 (d, 1H, J$_{HF}$=5.0 Hz, H2).

EXAMPLE 2

Synthesis of N-[tris(2,3,4,5,6-pentafluorophenyl)borane]3-methyl-3H-indole (A-4)

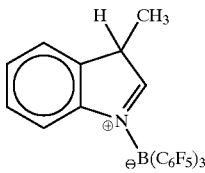

A solution of 3-methylindole (98%, 0.92 g, MW=131.18, 6.87 mmol) in 10 mL of dichloromethane was added at room temperature under nitrogen atmosphere to a solution of B(C$_6$F$_5$)$_3$ (BSC-382-4-0128, 99.4%, 3.53 g, MW=511.99, 6.85 mmol) in 15 mL of dichloromethane in a 50 mL Schlenk flask. Exothermicity was not observed. During the addition the color of the solution turned from light yellow to yellow. After 30 min stirring at room temperature, a $^1$H NMR analysis showed the presence of traces of unreacted 3-methylindole. Then 0.23 g (0.45 mmol) of tris(2,3,4,5,6-pentafluorophenyl)borane were added to complete the reaction. After overnight stirring, the solvent was removed in vacuo to give a white powder as product (yield 100%).

$^1$H NMR (CD$_2$Cl$_2$, δ, ppm): 1.61 (bs, 3H, CH$_3$); 4.31 (bs, 1H, H3); 7.35–7.67 (m, 4H, Ar); 8.69 (d, 1H, J$_{HF}$=5.3 Hz, H2).

$^1$H NMR (C$_6$D$_6$, δ, ppm): 0.65 (bs, 3H, CH$_3$); 2.74 (bs, 1H, H3); 6.62–6.84 (m, 3H, Ar); 7.53–7.62 (m, 1H, Ar); 7.91 (bs, 1H, H2, first diastereoisomer); 7.97 (bs, 1H, H2, second diastereoisomer).

$^{13}$C NMR (C$_6$D$_6$, δ, ppm): 11.72 (CH$_3$); 46.97 (C3); 111.18 (CH); 117.99 (C7); 123.76 (CH); 128.97 (CH); 138.32 (C3a); 146.52 (C7a); 179.29 (C2). The complex 3-methyl-3H-indole·B(C$_6$F$_5$)$_3$ shows two diastereoisomers at 10° C. in CD$_2$Cl$_2$. The ratio between the two diastereoisomers is 55:45 at 10° C. in CD$_2$Cl$_2$.

EXAMPLE 3

Synthesis of N-[tris(2,3,4,5,6-pentafluorophenyl)borane]2-methyl-3H-indole (A-3)

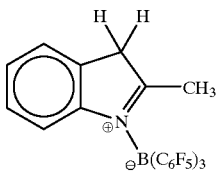

A solution of 2-methylindole (98%, 0.67 g, MW=131.18, 5.01 mmol) in 10 mL of dichloromethane was added at room temperature under nitrogen atmosphere to a solution of B(C$_6$F$_5$)$_3$ (99.4%, 2.60 g, MW=511.99, 5.05 mmol) in 15 mL of dichloromethane in a 50 mL Schlenk flask. Exothermicity was not observed. During the addition the color of the solution turned from light orange to orange. A $^1$H NMR analysis in CD$_2$Cl$_2$ showed quantitative conversion of the starting 2-methylindole after 1 h stirring at room temperature. The reaction mixture became a light pink suspension after 4 h stirring at room temperature. The stirring was continued overnight and then the suspension was filtered on a G3 frit. The residue on the frit was a white solid and resulted to be the desired product by $^1$H NMR analysis in C$_6$D$_6$ (2.16 g, yield 67.0%). The final complex is not fully soluble in CD$_2$Cl$_2$, while is fully soluble in C$_6$D$_6$.

$^1$H NMR (C$_6$D$_6$, δ, ppm): 1.70 (m, 3H, CH$_3$); 2.46 (AB system, 2H, J=25.63 Hz, H3'); 6.64–6.83 (m, 3H, Ar); 7.61–7.69 (m, 1H, Ar).

$^{13}$C NMR (C$_6$D$_6$, δ, ppm): 18.77 (dd, J$_{CF}$=9.20 Hz, J$_{CF}$=2.50 Hz, CH$_3$); 46.88 (C3); 117.74 (dd, J$_{CF}$=7.66 Hz, J$_{CF}$=1.84 Hz, C7); 123.83 (Ar); 127.75 (Ar); 128.15 (Ar); 130.79 (C3a); 150.44 (d, J$_{CF}$=3.98 Hz, C7a); 189.36 (C2). m.p.=204.3≧204.5 ° C.

EXAMPLE 4

Synthesis of N-(trichloroborane)3H-indole (A-20)

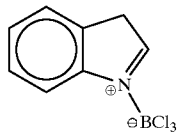

A solution of indole (99%, 1.79 g, MW=117.15, 15.13 mmol) in 20 mL of dichloromethane was added in 5 min at −20° C. under nitrogen atmosphere to a solution of BCl$_3$ (1M in heptane, 15 mL, 15.0 mmol) in 15 mL of dichloromethane in a 100 mL Schlenk flask. At the end of the addition a yellow suspension was formed. The reaction mixture was kept at −20° C. for 15 min and then allowed to warm up to room temperature. The color of the suspension turned slowly from yellow to pink. A $^1$H NMR analysis showed that the reaction was already complete after 1 h stirring at room temperature. After 4 h stirring at room temperature, the suspension was filtered on a G4 frit and the residue dried to give a pink powder, which resulted to be the desired product by $^1$H NMR analysis in CD$_2$Cl$_2$ (2.79 g, yield 79.4%).

$^1$H NMR (CD$_2$Cl$_2$, δ, ppm): 4.27 (bs, 2H, H3, H3'); 7.42–7.81 (m, 3H, Ar); 8.37–8.41 (m, 1H, Ar); 9.44–9.48 (m, 1H, H2).

$^1$H NMR (C$_2$D$_2$Cl$_4$, δ, ppm): 4.19 (bs, 2H, H3, H3'); 7.29–7.72 (m, 3H, Ar); 8.35–8.41 (m, 1H, Ar); 9.38–9.48 (m, 1H, H2). m.p.=184.8≧185.6 ° C.

The synthesis of N-(trichloroborane)3-hydroindole was carried out also by using the same conditions reported above, but adding the boron trichloride solution in eptane to the indole solution in dichloromethane, obtaining the same results.

EXAMPLE 5

Synthesis of N-[tris(2,3,4,5,6-pentafluorophenyl)borane]-2H-4,5,6,7-tetrahydroindole (A-13)

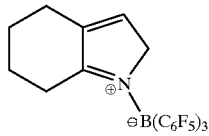

A solution of 4,5,6,7-tetrahydroindole (98%, 0.65 g, MW=121.18, 5.25 mmol) in 3 mL of dichloromethane was added at room temperature under nitrogen atmosphere to a solution of B(C$_6$F$_5$)$_3$ (99.4%, 2.69 g, MW=511.99, 5.25 mmol) in 15 mL of dichloromethane in a 25 mL Schlenk flask. A light exothermicity was observed. The reaction mixture was stirred for 30 min at room temperature and then the solvent was evaporated in vacuo to give a white powder as product. (yield 100%).

¹H NMR (CD₂Cl₂, δ, ppm): 7.34 (bm, 1H, H3); 4.85 (broad AB system, 2H, H2, H2'); 3.42–1.02 (bs, 8H, H4, H4', H5, H5', H6, H6', H7, H7').

¹³C NMR (CD₂Cl₂, δ, ppm): 21.74 (C5 and C6); 23.87 (C4); 29.76 (C7); 66.39 (d, C2, $J_{CF}$=10.4 Hz); 140.78 (C3a); 147.02 (C3); 186.25 (C7a).

EXAMPLE 6

Synthesis of N-[tris(2,3,4,5,6-pentafluorophenyl)borane]-2-methyl-6,10b-dihydroindeno[2,1-b]indole (A-21)

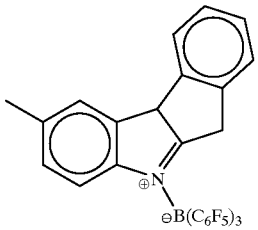

2-methyl-5,6-dihydroindeno[2,1-b]indole (1.77 g, MW=219.29, 8.1 mmol) was dissolved in 10 mL of CH₂Cl₂ and charged into a 50 mL Schlenk under nitrogen atmosphere. A solution of B(C₆F₅)₃ (4.14 g, MW=511.99, 8.1 mmol) in 25 mL of CH₂Cl₂ was added at room temperature under stirring. During the addition, the colour of the solution turned immediately from green to dark brown; exothermicity was not observed. The reaction mixture was stirred at room temperature for 1 h, then the solvent was removed in vacuo to give a brown solid as product (5.90 g). Yield =100%.

¹H NMR (CD₂Cl₂, δ, ppm): 2.46 (s, 3H, CH₃); 3.78 (d, 1H, J=20.1 Hz, CH₂); 4.23 (dd, 1H, J=20.1 Hz, J=3.0 Hz, CH₂); 5.86 (s, 1H, H10b); 7.16–7.69 (m, 7H, Ar).

¹³C NMR (CD₂Cl₂, δ, ppm): 21.33 (CH₃); 35.72 (d, CH₂, J=10.8 Hz); 62.88 (CH$_{10b}$); 117.88 (m); 124.04; 125.31; 125.80; 129.18; 129.48; 129.98; 133.20; 134.07; 139.25; 141.19; 149.24 (d, J=4.2 Hz); 200.03 (peak assigned by a DEPT experiment). m.p.=160.5° C.≧166.1° C.

EXAMPLE 7

Synthesis of N-[tris(2,3,4,5,6-pentafluorophenyl)borane] 5H-pyrrole (A-1)

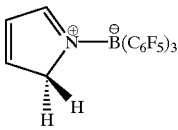

Procedure a)

A yellow-orange solution of pyrrole (98%, 0.35 g, MW=67.09, 5.11 mmol) in 10 mL of dichloromethane was added at room temperature under nitrogen atmosphere to a light yellow solution of B(C₆F₅)₃ (99.4%, 2.64 g, mw=511.99, 5.12 mmol) in 40 mL of dichloromethane in a 100 mL Schlenk flask. Exothermicity was not observed. The so-obtained yellow reaction mixture was stirred for 2 h at room temperature and then the solvent was removed in vacuo to give a white-light yellow powder as product (yield 100%).

¹H NMR (CD₂Cl₂, δ, ppm): 4.71 (bs, 2H, H5, H5'); 6.94 (dq, 1H J=5.48 Hz, J=1.08 Hz, H3); 7.90 (dq, 1H, J=5.48Hz, J=1.08 Hz,H4); 8.58 (m, 1H, J=1.08Hz, H2). ¹³C NMR (CD₂Cl₂, δ, ppm): 66.72 (m, C5); 128.61 (C3); 156.98 (C4); 172.04 (C2). NOESY (CD₂Cl₂): δ¹H/δ¹H=4.71/7.90 (H5H4), 7.90/6.94 (H4/H3), 6.94/8.58 (H3/H2). ¹H NMR (C₆D₆, δ, ppm): 3.70 (bs, 2H, H5, H5'); 5.62 (dq, 1H, J=6.16Hz, J=1.08Hz, H3); 6.51 (dq, 1H, J=6.16Hz, J=1.08 Hz, H4); 7.51 (m, 1H, J=1.08 Hz, H2).

¹³C NMR (C₆D₆, δ, ppm): 65.76 (m, C5); 127.38 (C3); 155.67 (C4); 171.38 (C2). NOESY (C₆D₆): δ¹H/δ¹H=3.70/6.51 (H5/H4), 6.51/5.62 (H4/H3), 5.62/7.51 (H3/H2). m.p.=187.0° C.–189.6 ° C.

Procedure b)

A light yellow solution of B(C₆F₅)₃ (1.182 g, MW=511.99, 2.31 mmol) in 8 mL of toluene was added at room temperature to a yellow solution of pyrrole (98%, 0.158 g, MW=67.09, 2.30 mmol) in 2 mL of toluene under nitrogen atmosphere in a 25 mL Schlenk flask. Exothermicity was not observed. The so-obtained yellow reaction mixture was stirred for 2 h at room temperature and then the solvent was removed in vacuo to give a yellow powder as product (1.255 g, purity 99.5%, yield 93.8%).

EXAMPLE 8

Synthesis of N-[tris(2,3,4,5,6-pentafluorophenyl)borane]-2, 4-dimethyl-5H-pyrrole (A-5)

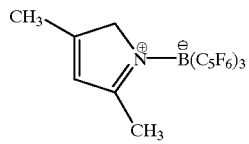

A yellow-orange solution of 2,4-dimethylpyrrole (97%, 0.564 g, MW=95.15, 5.75 mmol) in 5 mL of dichloromethane was added at room temperature under nitrogen atmosphere to a light yellow solution of B(C₆F₅)₃ (99.4%, 3.267 g, MW=511.99, 6.34 mmol) in 20 mL of dichloromethane in a 50 mL Schlenk flask. Exothermicity was not observed. The yellow reaction mixture was stirred for 20 h at room temperature and analyzed by ¹H NMR at different times. The final yellow solution was dried in vacuo giving a dark yellow powder as product (yield 100%).

¹H NMR (CD₂Cl₂, δ, ppm): 2.20 (t, 3H, J=2.74 Hz, CH₃ in 2); 2.29 (d, 3H, J=1.57 Hz, CH₃ in 4); 4.82 (broad AB system, 2H, H5, H5'); 6.41 (q, 1H, J=1.57 Hz, H3).

¹H NMR (C₆D₆, δ, ppm): 1.14 (d, 3H, J=1.47 Hz, CH₃ in 4); 1.41 (t, 3H, J=2.74 Hz, CH₃ in 2); 4.20 (bs, 2H, H5, H5'); 5.06 (bq, 1R J=1.47 Hz, H3).

¹³C NMR (CD₂Cl₂, δ, ppm): 14.56 (CH₃ in 4); 18.40 (CH3 in 2); 70.32 (C5); 128.65 (C3); 169.60 (C4); 185.40 (C2).

NOESY (CD₂Cl₂): δ¹H/δ¹H=4.82/2.29 (H5/CH₃ in 4), 2.29/6.41 (CH₃ in 4/H3), 6.41/2.20 (H3/CH₃ in 2).

m.p.=209.2≧211.8° C.

EXAMPLE 9
Synthesis of N-[tris(2,3,4,5,6-pentafluorophenyl)borane]-2,5-dimethyl-5H-pyrrole (A-6)

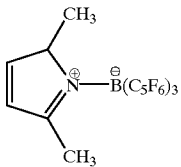

A pink solution of 2,5-dimethylpyrrole (98%, 0.313 g, MW=95.15, 3.22 mmol) in 8 mL of dichloromethane was added at room temperature under nitrogen atmosphere to a light yellow solution of $B(C_6F_5)_3$ (99.4%, 1.659 g, MW=511.99, 3.22 mmol) in 15 mL of dichloromethane in a 25 mL Schlenk flask. Exothermicity was not observed. The reaction mixture was stirred for 5 h at room temperature and analyzed by $^1H$ NMR at different times. The final light orange solution was dried in vacuo giving a yellow powder as product (1.878 g, yield 96.1%). The product resulted to be by NMR analysis a mixture of N-[tris(2,3,4,5,6-pentafluorophenyl)borane]-2,5-dimethyl-5-hydropyrrole (90%) and N-[tris(2,3,4,5,6-pentafluorophenyl)borane]-2,5-dimethyl-3-hydropyrrole (10%).

N-[tris(2,3,4,5,6-pentafluorophenyl)borane]-2,5-dimethyl-5-hydropyrrole:

$^1H$ NMR ($CD_2Cl_2$, δ, ppm): 1.23 (bt, 3H, J=7.14 Hz, $CH_3$ in 5); 2.20 (d, 3H, J=2.84 Hz, $CH_3$ in 2); 5.41 (bs, 1H, H5); 6.62 (dd, 1H, J=5.48 Hz, J=1.17 Hz, H3); 7.67 (m, 1H, J=5.48 Hz, H4).

$^1H$ NMR ($C_6D_6$, δ, ppm): 0.50 (m, 3H, $CH_3$ in 5); 1.29 (d, 3H, J=2.74 Hz, $CH_3$ in 2); 4.70 (bs, 1H, H5); 5.27 (dd, 1H, J=5.38 Hz, J=1.17 Hz, H3); 6.21 (dm, 1H, J=5.38 Hz, H4).

$^{13}C$ NMR ($CD_2Cl_2$, δ, ppm): 15.94 (d, $J_{CF}$=15.3 Hz, CH3 in 5); 19.36 (bs, $CH_3$ in 2); 77.02 (d, $J_{CF}$=15.3 Hz, CH5); 130.31 (C3); 161.43 (C4); 185.86 (d, $J_{CF}$=3.70 Hz C2).

NOESY ($CD_2Cl_2$): $δ^1H/δ^1H$=5.41/1.23 (H5/$CH_3$ in 5), 2.20/6.62 ($CH_3$ in 2/H3), 6.62/7.67 (H3/H4); 7.67/5.41 (H4/H5).

N-[tris(2,3,4,5,6-pentafluorophenyl)borane]-2,5-dimethyl-3-hydropyrrole:

$^1H$ NMR ($CD_2Cl_2$, δ, ppm): 2.03 (bs, 3H, $CH_3$); 2.44 (m, 3H, J=2.05 Hz, $CH_3$); 3.71 (broad AB system, 2H, J=26.8 Hz, H3, H3'); 6.10 (bs, 1H, H4).

$^1H$ NMR ($C_6D_6$, δ, ppm): 1.53 (m, 3H, $CH_3$); 1.61 (bs, 3H, $CH_3$); 2.09 (broad AB system, 2H, J=27.1 Hz, H3, H3'); 4.98 (bs, 1H, H4).

EXAMPLE 10
Synthesis of N-[tris(2,3,4,5,6-pentafluorophenyl)borane]-2-ethyl-5H-pyrrole (A-7)

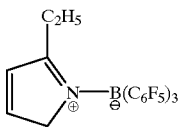

An orange solution of 2-ethylpyrrole (90%, 0.367 g, MW=95.15, 3.47 mmol) in 5 mL of dichloromethane was added at room temperature under nitrogen atmosphere to a light yellow solution of $B(C_6F_5)_3$ (99.4%, 1.80 g, MW=511.99, 3.49 mmol) in 15 mL of dichloromethane in a 25 mL Schlenk flask. During the addition the color of the solution turned immediately from orange to dark orange; exothermicity was not observed. The reaction mixture was stirred overnight at room temperature: a $^1H$ NMR analysis showed the presence of ca. 11% mol. of unreacted 2-ethylpyrrole. Then 0.21 g (0.41 mmol) of tris(2,3,4,5,6-pentafluorophenyl)borane were added to complete the reaction. After few minutes stirring, the solvent was removed in vacuo to give a white powder as product (yield 100%).

$^1H$ NMR ($CD_2Cl_2$, δ, ppm): 0.88 (t, 3H, J=7.43 Hz, $CH_3$); 2.67 (bm, 2H, $CH_2$); 4.99 (broad AB system, J=25.24 Hz, 2H, H5, H5'); 6.88 (dt, 1H, J=5.58 Hz, J=1.27 Hz, H3); 7.77 (d, 1H, J=5.58 Hz, H4).

$^1$NMR ($C_6D_6$, δ, ppm): 0.075 (t, 3H, J =7.43 Hz, $CH_3$); 2.00 (m, 2H, J =7.43 Hz, $CH_2$); 4.14 (broad AB system, J=25.14 Hz, 2H, H5, H5'$^5$); 5.54 (dt, 1H, J=5.48 Hz, J=1.27 Hz, H3); 6.31 (d, 1H, J=5.48 Hz, H4).

$^{13}C$ NMR ($CD_2Cl_2$, δ, ppm): 9.80 ($CH_3$); 25.48 ($CH_2$); 68.36 (m, C5); 130.30 (C3); 154.37 (C4); 189.38 (C2).

EXAMPLE 11
Synthesis of N-[tris(2,3,4,5,6-pentafluorophenyl)borane]-imidazole (A-9)

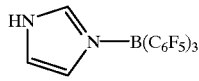

A colorless solution of imidazole in 5 mL of dichloromethane was added at room temperature under nitrogen atmosphere to a light yellow solution of $B(C_6F_5)_3$ (99.4%, 1.80 g, MW=511.99, 3.49 mmol) in 15 mL of dichloromethane in a 25 mL Schlenk flask. During the addition the color of the solution turned immediately from orange to dark orange; exothermicity was not observed. The reaction mixture was stirred 1 hour at room temperature then the solvent was removed in vacuo to give a white powder (2.60 g) as product (yield 100%).

$^1H$ NMR ($CD_2Cl_2$, δ, ppm): 7.18–7.24 (m, 2H, $H_4$ e $H_5$); 8.08 (s, 1H, $H_2$); 10.05 (bs, 1H, NH).

$^{13}C$ NMR ($CD_2Cl_2$, δ, ppm): 117.83 ($C_5$); 126.69 ($C_4$); 136.24 ($C_2$).

m.p.=214.9° C.—217.8° C.

EXAMPLE 12
Synthesis of N-[tris(2,3,4,5,6-pentafluorophenyl)borane]-pyrrolidine (A-10)

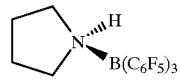

A solution of pyrrolidine (99.5%, 0.34 g, MW=71.12, 4.78 mmol) in 3 mL of dichloromethane was added at room temperature under nitrogen atmosphere to a solution of tris(2,3,4,5,6-pentafluorophenyl)borane (BSC-382-4-0128, 99.4%, 2.44 g, MW=511.99, 4.77 mmol) in 15 mL of dichloromethane in a 25 mL Schlenk flask. A light exothermicity was observed. The reaction mixture was stirred for 30 min at room temperature and then the solvent was evaporated in vacuo to give a white powder as product. (yield 100%).

$^1H$ NMR ($CD_2Cl_2$, δ, ppm): 6.30 (bs, 1H, NH); 3.44–3.54 (m, 2H, H2 and H5); 2.68–2.86 (m, 2H, H2 and H5); 1.84–2.09 (m, 4H, H3 and H4).

$^{13}C$ NMR ($CD_2Cl_2$, δ, ppm): 50.37 (C2 and C5); 23.86 (C3 and C4).

SYNTHESIS OF THE METALLOCENE COMPLEXES

Synthesis of bis(indenyl)zirconium dimethyl 29.6 mL of a solution of MeLi 1.6 M in $Et_2O$ (47.4 mmol) were added at room temperature to a solution of 3 g of indene (23.7 mmol, Aldrich, 91.8 %) in 30 mL of $Et_2O$, over a period of about 5 minutes (exothermic reaction). The mixture was stirred for 30 minutes to give an orange solution.

2.76 g of $ZrCl_4$ (11.84 mmol) were suspended in 30 mL of pentane. The $ZrCl_4$ slurry in pentane was quickly added to the Li salt solution in $Et_2O$ (exothermic reaction). The resulting reaction mixture was stirred for 2 hours and then brought to dryness under reduced pressure. The light brown solid obtained was extracted with 100 mL of pentane (Soxhlet, 4.5 hours) and then the filtrate was evaporated to dryness under reduced pressure to give 3.2 g (77 % yield) of a light yellow solid, which was characterized by $^1H$ NMR as chemically pure $Ind_2ZrMe_2$.

$^1$H-NMR ($C_6D_6$, δ, ppm): −0.78 (s, 6H, Zr-CH$_3$), 5.62 (t, 2H, Cp-H(2)), 5.80 (d, 4H Cp-H(1,3)); 6.87–6.92 (m, 4H, Ar), 7.19–7.23 (m, 4H, Ar).

Synthesis of bis(indenyl)hafnium dimethyl 32.4 mL of MeLi 1.6 M in $Et_2O$ (51.8 mmol) were added at −80° C. to a solution of 3 g of indene (Aldrich, 92 %, 23.7 mmol) in 30 mL of $Et_2O$, over a period of about 10 minutes. The reaction mixture was allowed to warm up slowly to room temperature and stirred for 4 hours. After this time the solution became orange from light-yellow. 1.41 mL of $TiCl_4$ (Aldrich, 99%, 12.8 mmol) were dissolved in 30 mL of pentane. Both the mixtures were cooled to −80° C. and the $TiCl_4$ solution was quickly added to the Li salt solution. The reaction mixture was allowed to warm up slowly to room temperature and stirred overnight with final formation of a dark brown suspension. The solvents were then removed under reduced pressure. The brown solid obtained was extracted in a Soxhlet apparatus with pentane. The filtrate was evaporated to dryness under reduced pressure to give 2.2 g of a dark-green powder (56 % yield).

$^1$H-NMR ($C_6D_6$, δ, ppm): −0.93 (s, 6H, Hf-CH$_3$); 5.57 (t, Cp-H(2), 2H), 5.69 (d, 4H, Cp-H(1,3)), 6.87–6.92 (m, 4H, Ar); 7.19-7.23 (m, 4H, Ar).

PREPARATION OF THE CATALYST SYSTEMS OF THE INVENTION

CATALYST SYSTEM 1

Bis(indenyl)zirconium dimethyl (1.0 g, MW=351.60, 2.84 mmol), prepared as described in the above-reported Synthesis 4, was dissolved in 20 mL of toluene in a 100 mL Schlenk under nitrogen atmosphere. A solution of 1.8 g of N-[tris(2,3,4,5,6-pentafluorophenyl)borane]3-hydroindole (MW=629.14, 2.86 mmol), prepared as described above, in 20 mL of toluene was added at room temperature under stirring. During the addition, methane evolution and a light exothermicity were observed. The reaction mixture was stirred at room temperature for 1 hour and 30 minutes, and then the solvent was removed in vacuo to give 2.74 g of an orange-red powder.

$^1$H-NMR ($C_6D_6$, δ, ppm): —0.82 (s, 3H, Zr-CH$_3$); 4.20 (s, 1H, CH); 5.05 (bs, 1H, CH); 5.20 (t, 1H, J=2.9 Hz, CH); 5.35–5.38 (m, 1H, CH); 5.52–5.55 (m, 1H, CH); 5.66 (t, 1H, J=2.5 Hz, CH); 5.83 (t, 1H, J=3.4 Hz, CH); 6.37–7.14 (m, 11H, Ar); 7.53 (bs, 1H, CH); 7.96 (d, 1H, J=8.3 Hz, CH).

$^{13}$C-NMR($C_6D_6$, δ, ppm): 50.48 (CH$_3$); 79.69 (CH); 100.96 (CH); 101.29 (CH); 103.15 (CH); 106.70 (CH); 115.39 (CH); 117.27 (CH); 118.78 (CH); 122.78; 123.82; 124.82; 125.03; 125.25; 125.37; 125.79; 126.44; 126.49; 126.79; 127.01; 135.94 (C); 145.62 (C); 155.91(CH) (peak assigned by a DEPT experiment). The remaining quaternary carbons were not completely assigned because probably covered from the peak of $C_6D_6$.

CATALYST SYSTEM 2

Bis(indenyl)hafnium dimethyl (0.50 g, Mw=438.87, 1.14 mmol), prepared as described above, were dissolved in 3 mL of toluene in a 15 mL Schlenk under nitrogen atmosphere. A solution of 0.72 g of N-[tris(2,3,4,5,6-pentafluorophenyl)borane]3-hydroindole ($M_w$=629.14, 1.14 mmol), prepared as described above, in 4 mL of toluene was added at room temperature under stirring. During the addition, methane evolution and a light exothermicity were observed. The reaction mixture was stirred at room temperature for 3 hours, then the solvent was removed in vacuo to give a red powder as product (1.20 g).

$^1$H-NMR ($C_6D_6$, δ, ppm): −0.85 (s, 3H, Hf-CH$_3$); 3.74 (s, 1H, CH); 4.99 (bs, 1H, CH); 5.20 (bs, 1H, CH); 5.28 (t, 1H, J=2.5 Hz, CH); 5.38 (bt, 1H, CH); 5.60 (bt, 1H, CH); 5.80 (t, 1H, J=3.0 Hz, CH); 6.36–7.14 (m, 11H, Ar); 7.62 (bs, 1H, CH); 7.95 (d, 1H, J=7.9 Hz, CH).

POLYMERIZATION

Polymer analysis

The carbon spectra were acquired at 120° C. either on a Bruker DPX-400 or a Bruker DPX-200 spectrometers, operating in the Fourier transform mode at 100.61 and MHz 50.323 MHz respectively.

The samples were dissolved in $C_2D_2Cl_4$ with a concentration of 8% w/v.

The spectra were acquired with a 90° pulse and 12 seconds of delay between pulses. About 1500 or 3000 transients were stored for each spectrum depending on the spectrometer. The peak of the $S_{\delta\delta}$ carbon (29.9 ppm) was used as reference. Nomenclature is according to Carman, C. J.; Harrington, R. A.; Wilkes, C. E. *Macromolecules* 1977, 10, 535 assignments of the peaks are according to Randall, J. C. *Macromol. Chem Phys.* 1989, C29, 201 and Tritto, I; Fan, Z.; Locatelli, P.; Sacchi, M.; Camurati, I.; Galimberti, M. *Macromolecules* 1995, 28, 3342.and the triad distribution was determined according to Kakugo, M.; Naito, Y., Mizunuma, K.; Miyatake, T. *Macromolecules* 1982, 15, 1150.

The intrinsic viscosity was measured in tetrahydronaphtalene (THN) at 135° C.

The polymer molecular weights were determined from the viscosity values.

Polymerization example 1

Ethylene polymerization

The polymerization test was carried out in a 1 L stainless-steel autoclave, thermostatted with $H_2O$/steam and purified by purging with ethylene at 80° C. Under ethylene purge, 513 mL technical hexane and 1 mmol TIBA were charged into the reactor, the temperature was brought to 80° C. and the reactor vented to remove residual nitrogen, then pressurized with ethylene up to 9.5 bar-g. 3.52 mg of the Catalyst System 1, prepared as described above, dissolved in 1.76 mL of toluene, was injected into the reactor by means of ethylene overpressure through a steel vial, and ethylene partial pressure was stabilized at 9.6 bar-a, ($P_{tot}$ 11 bar-a).

The polymerization was carried out at 80° C. for 1 hour, by maintaining a constant ethylene partial pressure, then stopped by pressurizing CO into the reactor and venting unreacted ethylene.

The polymer was isolated by filtration and dried under reduced pressure, at 60° C., thus obtaining 36.1 g of polyethylene, having an intrinsic viscosity of 4.3 dL/g.

Polymerization Examples 2–20

2 L of hexane were loaded into a 4.25-L stainless-steel stirred reactor at 30° C., followed by TIBA in hexane (amounts specified in Table 1) as a scavenger. Propylene and ethylene were then pressurized into the reactor, to reach the composition of 1.2 wt % ethylene and 22.8 wt % propylene, and the temperature of the reactor was then raised up to 50° C.

The catalytic complex was prepared by quickly mixing 5 mg of bis indenyl zirconium dichloride in 5 ml of toluene, one equivalent of the cocatalyst dissolved in toluene (500 equivalents are used for MAO), and if required 2 mL of Triisobutyl aluminum 0.5 M in hexane (TIBA) as indicated in table 1.

The polymerization was started by injecting the toluene solution containing the toluene catalyst/cocatalyst solution into the autoclave, by means of ethylene overpressure, then the temperature was maintained at 50° C., and ethylene was continuously fed into the reactor in order to maintain a constant pressure. After 40 g of ethylene were added, the polymerization was stopped by pressurizing 1.5 L of CO into the reactor, venting and cooling the reactor(inactive tests are stopped after 60 min). The ethylene/propylene amorphous copolymer was recovered from the hexane solution by precipitation in acetone, followed by drying under reduced atmosphere at 70° C. for 4 hours.

The properties of the copolymers are listed in Table 1

TABLE 1

| Ex. | Cocat | TIBA mmol premix (b) | TIBA mmol in solvent | aging(a) min | time(d) min | kg/$g_{cat}$ | kg/($g_{cat}$ × h) | ethylene % wt (NMR) | I.V. dL/g |
|---|---|---|---|---|---|---|---|---|---|
| 2* | MAO(b) | — | 2 | 10 | 15 | 13.0 | 52.0 | 81.3 | 1.7 |
| 3* | B($C_6F_5$)$_3$(c) | — | 3 | 1 | 60 | none | — | — | — |
| 4* | B($C_6F_5$)$_3$(c) | — | 6 | 1 | 19 | 12.8 | 40.4 | 77.8 | 2.2 |
| 5* | B($C_6F_5$)$_3$(c) | — | 6 | 30 | 60 | none | — | — | — |
| 6* | B($C_6F_5$)$_3$(c) | 1 | 5 | 30 | 60 | none | — | — | — |
| 7 | A-1 | | 3 | 1 | 60 | 10.8 | 10.8 | 81.0 | 2.9 |
| 8 | A-1 | | 6 | 1 | 14 | 13.0 | 55.7 | 78.4 | 2.2 |
| 9 | A-2 | | 3 | 1 | 21 | 13.8 | 39.4 | 77.5 | 1.9 |
| 10 | A-2 | | 6 | 1 | 11 | 16.4 | 89.5 | 71.8 | 1.7 |
| 11 | A-2 | | 6 | 30 | 13 | 14.6 | 67.4 | 77.7 | 2.1 |
| 12 | A-2 | 1 | 5 | 30 | 8 | 13.8 | 103.5 | 71.9 | 1.7 |
| 13 | A-2 | 2 | 2 | 5 | 8 | 14.2 | 106.5 | 75.0 | — |
| 14 | A-3 | | 3 | 1 | 40 | 11.4 | 17.1 | 79.8 | 2.5 |
| 15 | A-4 | | 6 | 1 | 24 | 13.0 | 32.5 | 75.3 | 2.0 |
| 16 | A-4 | | 6 | 30 | 34 | 12.4 | 21.9 | 78.3 | 2.3 |
| 17 | A-5 | | 3 | 1 | 68 | 11.0 | 9.7 | 80.9 | 2.66 |
| 18 | A-6 | | 3 | 1 | 14 | 15.0 | 64.3 | 78.6 | 2.14 |
| 19* | A-9 | | 3 | 1 | 60 | 0.8 | 0.8 | — | — |
| 20* | A-10 | | 6 | 1 | 60 | 0.9 | 0.9 | 80.5 | 3.2 |

(a)time of aging at room temperature of the catalyst/cocatalyst mixture.
(b) (b)MAO (methyl alumoxane) purchased by Witco.
(c)purchased from Boulder.
*comparative example.

What is claimed is:

1. An organometallic compound obtained by contacting
a) a compound having following formula (I):

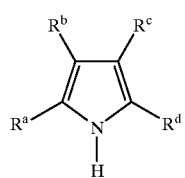

(I)

wherein $R^a$, $R^b$, $R^c$ and $R^d$, equal to or different from each other, are selected from the group consisting of hydrogen, halogen, linear or branched, saturated or unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^a$, $R^b$, $R^c$ and $R^d$ form one or more $C_4$–$C_7$ rings, optionally containing O, S, N, P or Si atoms, that can bear substituents; with
b) a Lewis acid of formula (II)

$$MtR^1_3 \qquad (II)$$

wherein Mt is a metal belonging to Group 13 of the Periodic Table of the Elements; $R^1$, equal to or different from each other, are selected from the group consisting of halogen, halogenated $C_6$–$C_{20}$ aryl and halogenated $C_7$–$C_{20}$ alkylaryl groups; two $R^1$ groups optionally form with the metal Mt one condensed ring.

2. The organometallic compound according to claim 1 wherein Mt is B or Al; the substituents $R^1$ are selected from the group consisting of fluoro, $C_6F_5$, $C_6F_4H$, $C_6F_3H_2$, $C_6H_3(CF_3)_2$, perfluoro-biphenyl, heptafluoro-naphthyl, hexafluoro-naphthyl and pentafluoro-naphthyl.

3. The organometallic compound according to claim 1, having formula (III)

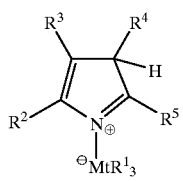

(III)

wherein Mt is a metal belonging to Group 13 of the Periodic Table of the Elements; $R^1$, equal to or different from each other, are selected from the group consisting of halogen, halogenated $C_6$–$C_{20}$ aryl and halogenated $C_7$–$C_{20}$ alkylaryl groups; two $R^1$ groups optionally form with the metal Mt one condensed ring;
and the substituents $R^5$, $R^4$, $R^3$ and $R^2$, equal to or different from each other, are selected from the group consisting of hydrogen, halogen, linear or branched, saturated or unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^2$–$R^5$ form one or more $C_4$–$C_7$ rings, optionally containing O, S, N, P or Si atoms; with the proviso that at least one of the substituents $R^5$, $R^4$, $R^3$ and $R^2$ is different from hydrogen.

4. The organometallic compound according to claim 3, wherein Mt is B or Al; the substituents $R^1$ equal to or different from each other, are selected from the group consisting of fluoro, $C_6F_5$, $C_6F_4H$, $C_6F_3H_2$, $C_6H_3(CF_3)_2$, perfluoro-biphenyl, heptafluoro-naphthyl, hexafluoro-naphthyl and pentafluoro-naphthyl; at least one of the substituents $R^5$ and $R^4$ is a $C_6$–$C_{20}$ aryl, $C_7$–$C_{20}$ arylalkyl or $C_7$–$C_{20}$ alkylaryl groups, optionally containing O, S, N, P, Si or halogen atoms, or together $R^5$ and $R^4$ form an aromatic $C_5$–$C_7$ ring optionally containing O, S, N, P or Si atoms, that can bear substituents.

5. The organometallic compound according to claim 3, having formula (V):

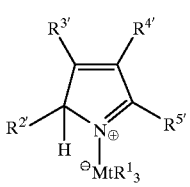

(V)

wherein
B is a boron atom;
the substituents $R^1$, $R^3$ and $R^2$ have the meaning reported in claim 3 and the substituents $R^6$, the same or different from each other, are selected from the group consisting of hydrogen, halogen, linear or branched, saturated or unsaturated, $C_1$–$C_{10}$ alkyl, $C_6$–$C_{20}$ aryl, $C_7$–$C_{20}$ arylalkyl and $C_7$–$C_{20}$ alkylaryl groups optionally containing O, S, N, P, Si or halogen atoms, or two or more adjacent substituents $R^6$ form one or more $C_4$–$C_7$ rings, optionally containing O, S, N, P or Si atoms, that can bear substituents.

6. The organometallic compound according to claim 3, having formula (VI):

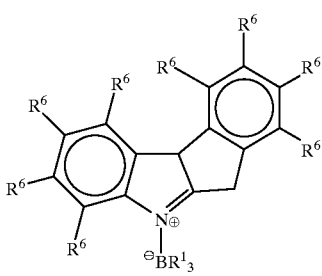

(VI)

wherein the substituent $R^1$ have the meaning reported in claim 3 and the substituents $R^6$, the same or different from each other, are selected from the group consisting of hydrogen, halogen, linear or branched, saturated or unsaturated, $C_1$–$C_{10}$ alkyl, $C_6$–$C_{20}$ aryl, $C_7$–$C_{20}$ arylalkyl and $C_7$–$C_{20}$ alkylaryl groups optionally containing O, S, N, P, Si or halogen atoms, or two or more adjacent substituents $R^6$ form one or more $C_4$–$C_7$ rings, optionally containing O, S, N, P or Si atoms, that can bear substituents.

7. The organometallic compound according to claim 1, having formula (IV):

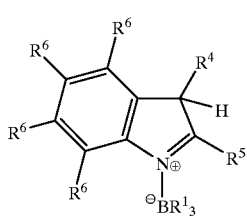

(IV)

wherein
Mt and $R^1$ have the meanings reported in claim 1;
the substituents $R^{2'}$, $R^{3'}$, $R^{4'}$ and $R^{5'}$, equal to or different from each other, are selected from the group consisting of hydrogen, halogen, linear or branched, saturated or unsaturated, $C_1$–$C_{10}$ alkyl, $C_6$–$C_{20}$ aryl, $C_7$–$C_{20}$ arylalkyl and $C_7$–$C_{20}$ alkylaryl groups, optionally containing O, S, N, P, Si or halogen atoms, or two or more adjacent substituents $R^{2'}$, $R^{3'}$, $R^{4'}$ and $R^{5'}$ form one or more $C_4$–$C_7$ rings optionally containing O, S, N, P or Si atoms, that can bear substituents; said rings are aliphatic and optionally contain double bonds, with the proviso that said rings are not aromatic.

8. The organometallic compound according to claim 7, wherein the substituents $R^{2'}$, $R^{3'}$, $R^{4'}$ and $R^{5'}$, equal to or different from each other, are selected from the group consisting of hydrogen, linear or branched, saturated or unsaturated, $C_1$–$C_{10}$ alkyl, optionally containing O, S, N, P or Si atoms, or two or more adjacent substituents $R^{2'}$, $R^{3'}$, $R^{4'}$ and $R^{5'}$ form one or more $C_4$–$C_7$ rings optionally containing O, S, N, P or Si atoms, that can bear substituents; said rings are aliphatic and optionally contains double bonds, with the proviso that said rings are not aromatic.

9. The organometallic compound according to claim 8, having formula (VII):

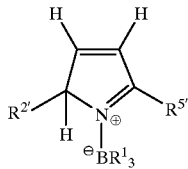

(VII)

wherein the substituents $R^1$ have the meaning described in claim 1 and the substituents $R^{2'}$ and $R^{5'}$, equal to or different from each other, are $C_1$–$C_{20}$ alkyl.

10. A process for preparing the organometallic compounds according to claim 1 comprising the step of reacting, about in stoichiometric amounts, a compound having the formula (I):

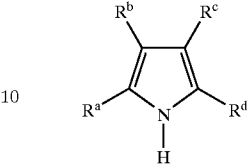

(I)

with a Lewis acid of formula (II)

$$MtR^1_3 \qquad (II).$$

* * * * *